United States Patent [19]

Furuya et al.

[11] Patent Number: 5,675,031
[45] Date of Patent: Oct. 7, 1997

[54] 4-HYDROXY-2-CYCLOPENTENONE DERIVATIVES AND ANTICANCER AGENT AND BONE FORMATION ACCELERATOR CONTAINING THE SAME

[75] Inventors: Minoru Furuya, Fuchu; Satoshi Sugiura; Atsuo Hazato, both of Hino, all of Japan

[73] Assignee: Teijin Limited, Osaka, Japan

[21] Appl. No.: 397,176

[22] PCT Filed: Sep. 7, 1993

[86] PCT No.: PCT/JP93/01266

§ 371 Date: Mar. 8, 1995

§ 102(e) Date: Mar. 8, 1995

[87] PCT Pub. No.: WO94/05619

PCT Pub. Date: Mar. 17, 1994

[30] Foreign Application Priority Data

Sep. 10, 1992 [JP] Japan ................ 4-241998

[51] Int. Cl.$^6$ ................ C07C 69/76
[52] U.S. Cl. ................ 560/53; 556/437
[58] Field of Search ................ 560/53; 556/437

[56] References Cited

FOREIGN PATENT DOCUMENTS

| 0106576 | 4/1984 | European Pat. Off. ...... C07C 69/738 |
| 131441 | 1/1985 | European Pat. Off. ...... C07C 49/687 |
| 58-216155 | 12/1983 | Japan ................ C07C 177/00 |
| 113036 | 1/1989 | Japan ................ C07B 37/04 |
| 2138118 | 5/1990 | Japan ................ A61K 31/12 |
| 9105766 | 5/1991 | Japan ................ C07C 317/24 |

OTHER PUBLICATIONS

Chemical Abstracts 111:232451 1986.

Proc. Natl. Acad. Sci. USA, vol. 81, pp. 1317–1321, Mar. 1984, Biochemistry.

*Primary Examiner*—Paul J. Killos
*Attorney, Agent, or Firm*—Sughrue, Mion, Zinn, Macpeak and Seas

[57] ABSTRACT

Specific optically active 4- hydroxy-2-cyclopentenone derivatives and mixtures thereof having the formula (I):

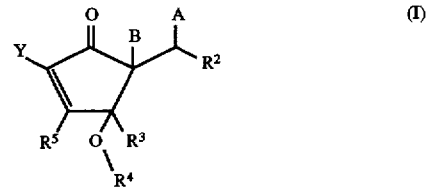

and an anticancer-agent and a bone formation accelerator containing the same as effective active ingredients.

10 Claims, No Drawings

4-HYDROXY-2-CYCLOPENTENONE DERIVATIVES AND ANTICANCER AGENT AND BONE FORMATION ACCELERATOR CONTAINING THE SAME

TECHNICAL FIELD

The present invention relates to 2-cyclopentenone derivatives and mixtures thereof, more specifically relates to novel 4-hydroxy-2-cyclopentenone derivatives and mixtures thereof having superior pharmacological activities such as an anticancer activity and bone formation activity and an anticancer agent and a bone formation accelerator containing the same as an active ingredient.

BACKGROUND ART

Prostaglandins are compounds having specific biological activities, such as a platelet agglutination inhibitory activity, a vasodepressor activity, etc., and are useful naturally occurring substances which have been used in recent years in the field of medicine as therapeutic agents for diseases of peripheral cardiovascular system. Among the prostaglandins, prostaglandin A compounds are known as a prostaglandin having a double bond in the cyclopentane ring. For example, European Published Application No. 0106576 (published Apr. 25 , 1984) discloses a 4,5-substituted 2-cyclopentenone compounds including prostaglandin A compounds, which include a 5-alkylidene-4-substituted-2-cyclopentenone having the following formula:

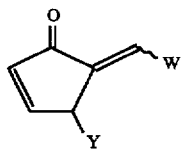

wherein W represents a $C_1$ to $C_{12}$ hydrocarbon group which may be substituted and Y represents a $C_1$ to $C_{12}$ hydrocarbon group which may be substituted and a 5-(1-hydroxyhydrocarbon)-4-substituted-2-cyclopentenone having the following formula:

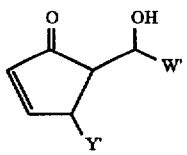

wherein W' and Y' are the same as W and Y, respectively. Further, it is disclosed therein that these compounds are effective against malignant tumors.

Further, European Published Application No. 0131441 (published Jan. 16, 1985) discloses 5-alkylidene-2-halo-4-substituted-2-cyclopentenone compounds having the following formula:

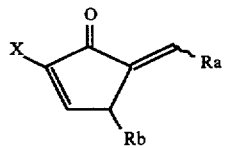

wherein $R_a$ represents a substituted or unsubstituted $C_1$–$C_{12}$ hydrocarbon or a substituted or unsubstituted phenyl group; Rb represents a substituted or unsubstituted $C_1$–$C_{12}$ hydrocarbon group; and X represents a halogen atom. It is further disclosed that these compounds are similarly effective for malignant tumors.

Furthermore, it is also known in the art that prostaglandin D and J compounds, which are different from prostaglandin A compounds, are useful as antitumor agents (Japanese Unexamined Patent Publication (Kokai) No. 58-216155 and Proc. Natl. Acad. Sci. U.S.A.), 81, 1317–1321 (1984)).

The present inventors clarified in European Published Application No. 338796 and International Disclosure No. WO91/05766 that there are an antitumor activity and bone-formation accelerating activity in 2-cyclopentenone compounds having the following formula and having a group with sulfur atom bonded at the 2-position:

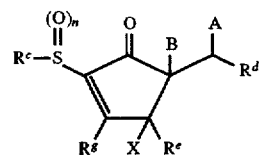

wherein, $R^c$ represents a substituted or unsubstituted (i) $C_1$–$C_{10}$ aliphatic hydrocarbon group, (ii) a $C_4$–$C_{10}$ alicyclic hydrocarbon group, (iii) a $C_6$–$C_{10}$ aromatic hydrocarbon group, or (iv) a $C_1$–$C_9$ heterocyclic group, $R^d$ represents a substituted or unsubstituted (i) $C_1$–$C_{10}$ aliphatic hydrocarbon group, (ii) a $C_4$–$C_{10}$ alicyclic hydrocarbon group, (iii) a $C_6$–$C_{10}$ aromatic hydrocarbon group, or (iv) a $C_1$–$C_9$ heterocyclic group, $R^e$ represents a hydrogen atom or a substituted or unsubstituted (i) $C_1$–$C_{10}$ aliphatic hydrocarbon group, (ii) $C_4$–$C_{10}$ alicyclic hydrocarbon group, or (iii) $C_6$–$C_{10}$ aromatic hydrocarbon group, X represents a hydrogen atom or —$OR^f$ wherein $R^f$ represents a hydrogen atom, $C_1$–$C_4$ alkyl group, $C_2$–$C_7$ acyl group, $C_2$–$C_5$ alkoxycarbonyl group, tri ($C_1$–$C_7$) hydrocarbon silyl group or a group which forms an acetal bond together with the oxygen atom to which the $R^f$ bonds or, when $R^e$ bonds, by a double bond, to the carbon atom bonded to $R^e$, there is no X, $R^g$ is a hydrogen atom or a substituted or unsubstituted (i) $C_1$–$C_{10}$ aliphatic hydrocarbon group or (ii) $C_4$–$C_{10}$ alicyclic hydrocarbon group, when A represents a hydroxyl group, $C_2$–$C_7$ acyloxyl group, $C_2$–$C_5$ alkoxycarbonyloxyl group, or $C_1$–$C_7$ sulfonyloxyl group or

B is a hydrogen atom or A and B together represent a single bond, and m and n are the same or different and represents 0, 1, or 2.

The present inventors found, as shown in Japanese Unexamined Patent Publication (Kokai) No. 62-96438, that 4-hydroxy-2-cyclopentenone compounds having the following formula:

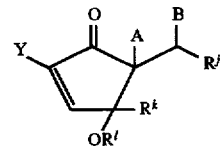

wherein Y represents a hydrogen atom or halogen atom, A and B represent a combination where A is a hydrogen atom and B is a hydroxyl group or bond together to form a single bond, $R^j$ represents a substituted or unsubstituted $C_1$–$C_{10}$ alkyl group, alkenyl group or alkynyl group, $R^k$ represents a substituted or unsubstituted $C_1$–$C_{10}$ alkyl group, alkenyl group or alkynyl group, and $R^1$ represents a hydrogen atom or a protecting group for a hydroxyl group, where $R^k$ does not represent 2-octenyl, 8-acetoxy-2-octenyl or 2,5-octadienyl were useful for the treatment of malignant tumors. Further, Japanese Unexamined Patent Publication (Kokai) No. 2-138118 and Japanese Patent Application No. 1-13036 disclose that these compounds have the bone formation accelerating activities.

DISCLOSURE OF THE INVENTION

Accordingly, the object of the present invention is to provide not only the above-mentioned group of compounds, but also further effective optically active 4-hydroxy-2-cyclopentenone derivatives and mixtures thereof.

Another object of the present invention is to provide an anticancer agent containing, as an active ingredient, optically active 4-hydroxy-2-cyclopentenone derivatives and mixtures thereof.

A further object of the present invention is to provide a bone formation accelerator containing as an active ingredient, optically active 4-hydroxy-2-cyclopentenone derivatives and mixtures thereof.

Other objects and advantages of the present invention will be apparent from the following explanation.

In accordance with the present invention, there are provided optically active 4-hydroxy-2-cyclopentenone derivatives or thereof having the following formula (I):

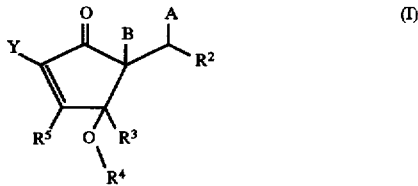

wherein Y represents a hydrogen atom or halogen atom, A and B are such that B is a hydrogen atom and A is a hydroxyl group, $C_2$–$C_7$ acyloxyl group, $C_2$–$C_5$ alkoxycarbonyloxyl group, or $C_1$–$C_7$ sulfonyloxyl group or A and B together form a single bond, $R^2$ represents a substituted or unsubstituted (i) $C_4$–$C_{10}$ alicyclic hydrocarbon group, (ii) $C_6$–$C_{10}$ aromatic hydrocarbon group, or (iii) $C_1$–$C_9$ heterocyclic group, $R^3$ represents a substituted or unsubstituted (i) $C_1$–$C_{10}$ aliphatic hydrocarbon group, (ii) $C_4$–$C_{10}$ alicyclic hydrocarbon group, (iii) $C_6$–$C_{10}$ aromatic hydrocarbon group, or (iv) hydrogen atom, $R^4$ represents a hydrogen atom, $C_1$–$C_4$ alkyl group, $C_2$–$C_7$ acyl group, $C_2$–$C_5$ alkoxycarbonyl group, tri ($C_1$–$C_7$) hydrocarbon silyl group or a group forming an acetal bond together with the oxygen atom to which $R^4$ is bonded. $R^5$ represents a substituted or unsubstituted (i) $C_1$–$C_{10}$ aliphatic hydrocarbon group, (ii) $C_4$–$C_{10}$ alicyclic hydrocarbon group, or (iii) a hydrogen atom, and mixtures thereof.

In accordance with the present invention, there are further provided an anticancer agent and a bone formation accelerator containing these compounds as active ingredients.

BEST MODE FOR CARRYING OUT THE INVENTION

In the above-mentioned formula (I), Y represents a hydrogen atom or halogen atom. The halogen includes, for example, fluorine, chlorine, bromine, or iodine and fluorine or chlorine is preferable. Y especially preferably includes a hydrogen atom or chlorine atom.

In the above-mentioned formula (I), A and B represent a combination in which B is a hydrogen atom and A is a hydroxyl group, $C_2$–$C_7$ acyloxyl group, $C_2$–$C_5$ alkoxycarbonyloxyl group, or $C_1$–$C_7$ sulfonyloxyl group or bond together to form a single bond.

When A and B bond together to form a single bond, the above formula (I) shows optically active 4-hydroxy-2-cyclopentenone derivatives and mixtures thereof having the following formula (I-1):

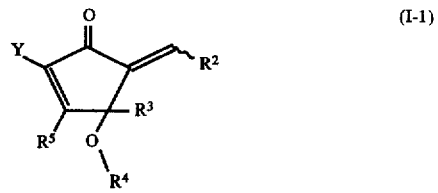

wherein the wavy line ⁓ shows that a substituent bonding to the double bond is an E configuration or Z configuration or a mixture thereof in any ratio and Y, $R^2$, $R^3$, $R^4$, and $R^5$ are the same as defined above.

Further, when B is a hydrogen atom, the above-mentioned formula (I) shows optically active 4-hydroxy-2-cyclopentenone derivatives and mixtures thereof having the following formula ( I-2 ):

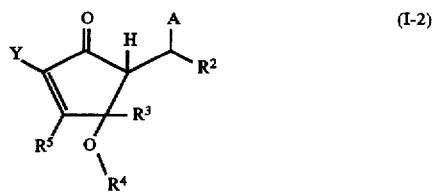

wherein $A'$ represents a hydroxyl group, $C_2$–$C_7$ acyloxyl group, $C_2$–$C_5$ alkoxycarbonyloxyl group, or $C_1$–$C_7$ sulfonyloxyl group and Y, $R^2$, $R^3$, $R^4$, and $R^5$ are the same as defined above.

When A is a $C_2$–$C_7$ acyloxyl group in the above-mentioned formula (I), examples of such $C_2$–$C_7$ acyloxyl group are an acetoxyl, propionyloxyl, isopropionyloxyl, butyryloxyl, isobutyryloxyl, s-butyryloxyl, valeryloxyl, isovaleryloxyl, hexanoyloxyl, heptanoytoxyl, and benzoyloxyl group.

When A represents $C_2$–$C_5$ alkoxycarbonyloxyl group in the above-mentioned formula (I), examples of the $C_2$–$C_5$ alkoxycarbonyloxyl group are a methoxycarbonyloxyl, ethoxycarbonyloxyl, propoxycarbonyloxyl, isopropoxycarbonyloxyl, butoxycarbonyloxyl, isobutoxycarbonyloxyl, s-butoxycarbonyloxyl, and t-butoxycarbonyloxyl group.

When A represents a $C_1$–$C_7$ sulfonyloxyl group in the above-mentioned formula (I), as such $C_1$–$C_7$ sulfonyloxyl group, there may be mentioned a $C_1$–$C_4$ alkylsulfonyloxyl group, which may be substituted with a halogen atom, a substituted or unsubstituted phenylsulfonyloxyl group, or a substituted or unsubstituted phenyl ($C_1$–$C_2$) alkylsulfonyloxyl group. As the $C_1$–$C_2$ alkylsulfonyloxyl group, which may be substituted with a halogen atom, mention may be made of a methanesulfonyloxyl, ethanesulfonyloxyl, butanesulfonyloxyl, t-butanesulfonyloxyl, chloromethanesulfonyloxyl, dichloromethanesulfonyloxyl, trifluoromethanesulfonyloxyl, nonafluorobutanesulfonyloxyl group, etc. Examples of the substituted or unsubstituted phenylsulfonyloxyl group are a benzenesulfonyloxyl, p-bromobenzenesulfonyloxyl, toluenesulfonyloxyl group, etc. Examples of the substituted or unsubstituted phenyl ($C_1$–$C_2$) alkylsulfonyloxyl group are the benzylsulfonyloxyl, α-phenethylsulfonyloxyl, β-phenethylsulfonyloxyl group, etc.

$R^2$ in the above-mentioned formula (I) is a substituted or unsubstituted (i) $C_4$–$C_{10}$ alicyclic hydrocarbon group, (ii) $C_6$–$C_{10}$ aromatic hydrocarbon group, or (iii) $C_1$–$C_9$ heterocyclic group. As the preferable group of $R^2$, mention may be made of a substituted or unsubstituted $C_6$–$C_{10}$ aromatic hydrocarbon group.

As examples of the unsubstituted $C_4$–$C_{10}$ alicyclic hydrocarbon group of $R^2$, mention may be made of a cyclobutyl, cyclopentyl, cyclohexyl, 1-cyclohexenyl, 3-cyclohexenyl, 4-cyclohexenyl, cycloheptyl, cyclooctyl, or bicyclo [4.4.0] decane-2-yl group and other monocyclic or bicyclic groups. As examples of the unsubstituted $C_6$–$C_{10}$ aromatic hydrocarbon group of $R^2$, mention may be made of the phenyl, 1-napthyl, and 2-napthyl group. As examples of the unsubstituted $C_1$–$C_9$ heterocyclic group of $R^2$, mention may be made of the furyl, thienyl, pyrrolyl, oxazolyl, isooxazolyl, thiazolyl, isothiazolyl, imidazolyl, pyrazolyl, triazolyl, tetrazolyl, pyranyl, pyridyl, pyradinyl, pyrimidinyl, benzofuranyl, indolyl, benzimidazolyl, benzothiazolyl, benzoxazolyl, quinolyl, isoquinolyl, quinazolyl, purinyl, pteridinyl, morpholinyl, and piperidinyl group and other monocyclic or bicyclic groups having an oxygen, nitrogen, or sulfur atom.

When $R^2$ represents a (i) $C_4$–$C_{10}$ alicyclic hydrocarbon group, (ii) $C_6$–$C_{10}$ aromatic hydrocarbon group, or (iii) $C_1$–$C_9$ heterocyclic group having a substituent, as the substituent, mention may be made of the following (i) to (viii):

(i) halogen atom (ii) oxo group (iii) cyano group (iv) nitro group (v) —COOR$^{62}$ wherein R$^{62}$ represents a hydrogen atom; 1 equivalent of cations; sugar residue; or a $C_1$–$C_{10}$ aliphatic hydrocarbon group which may be substituted with a halogen atom, oxo group, hydroxyl group, nitro group, tri ($C_1$–$C_7$) hydrocarbon silyloxyl group, $C_2$–$C_7$ acyloxyl group, $C_2$–$C_5$ alkoxycarbonyl group, $C_1$–$C_4$ alkoxyl group, $C_4$–$C_{10}$ alicyclic hydrocarbon group, and $C_6$–$C_{10}$ aromatic hydrocarbon group.

(vi) —OR$^{72}$ wherein R$^{72}$ represents a hydrogen atom; $C_1$–$C_4$ alkyl group; $C_2$–$C_7$ acyl group; $C_2$–$C_5$ alkoxycarbonyl group; tri ($C_1$–$C_7$) hydrocarbon silyl group; a group forming an acetal bond with the oxygen atom to which R$^{72}$ is bonded; a $C_1$–$C_{10}$ aliphatic hydrocarbon group or $C_4$–$C_{10}$ alicyclic hydrocarbon group which may be substituted with a halogen atom, oxo group, hydroxyl group, nitro group, carboxyl group, cyano group, tri ($C_1$–$C_7$) hydrocarbon silyloxyl group, $C_2$–$C_7$ acyloxyl group, $C_2$–$C_5$ alkoxycarbonyloxyl group, $C_1$–$C_4$ alkoxyl group, $C_2$–$C_7$ acyl group, $C_2$–$C_5$ alkoxycarbonyl group, or $C_6$–$C_{10}$ aromatic hydrocarbon group; or a $C_6$–$C_{10}$ aromatic hydrocarbon group which may be substituted with a halogen atom, hydroxyl group, nitro group, carboxyl group, cyano group, tri ($C_1$–$C_7$) hydrocarbon silyloxyl group, $C_2$–$C_7$ acyloxyl group, $C_2$–$C_5$ alkoxycarbonyloxyl group, $C_1$–$C_4$ alkoxyl group, $C_2$–$C_7$ acyl group, $C_2$–$C_5$ alkoxycarbonyl group, or $C_1$–$C_4$ alkyl group.

(vii) —CONR$^{82}$R$^{820}$ wherein R$^{82}$ and R$^{820}$ are the same or different and represent a hydrogen atom; a $C_1$–$C_{10}$ aliphatic hydrocarbon group or $C_4$–$C_{10}$ alicyclic hydrocarbon group which may be substituted with a halogen atom, oxo group, hydroxyl group, nitro group, carboxyl group, tri ($C_1$–$C_7$) hydrocarbon silyloxyl group, $C_2$–$C_7$ acyloxyl group, $C_2$–$C_5$ alkoxycarbonyloxyl group, $C_1$–$C_4$ alkoxyl group, $C_2$–$C_7$ acyl group, $C_2$–$C_5$ alkoxycarbonyl group, or $C_6$–$C_{10}$ aromatic hydrocarbon group; a $C_6$–$C_{10}$ aromatic hydrocarbon group which may be substituted with a halogen atom, hydroxyl group, nitro group, carboxyl group, cyano group, tri ($C_1$–$C_7$) hydrocarbon silyloxyl group, $C_2$–$C_7$ acyloxyl group, $C_2$–$C_5$ alkoxycarbonyloxyl group, $C_1$–$C_4$ alkoxyl group, $C_2$–$C_7$ acyl group, $C_2$–$C_5$ alkoxycarbonyl group, or $C_1$–$C_4$ alkyl group; or group where R$^{82}$ and R$^{820}$ bond with each other to form a 5- or 6-membered ring.

(viii) —NR$^{92}$R$^{920}$ wherein R$^{92}$ and R$^{920}$ are the same or different and represent a hydrogen atom; a $C_1$–$C_{10}$ aliphatic hydrocarbon group or $C_4$–$C_{10}$ alicyclic hydrocarbon group which may be substituted with a halogen atom, oxo group, hydroxyl group, nitro group, carboxyl group, tri ($C_1$–$C_7$) hydrocarbon silyloxyl group, $C_2$–$C_7$ acyloxyl group, $C_2$–$C_5$ alkoxycarbonyloxyl group, $C_1$–$C_4$ alkoxyl group, $C_2$–C; acyl group, $C_2$–$C_5$ alkoxycarbonyl group, or $C_6$–$C_{10}$ aromatic hydrocarbon group; a $C_6$–$C_{10}$ aromatic hydrocarbon group which may be substituted with a halogen atom, hydroxyl group, nitro group, carboxyl group, cyano group, tri ($C_1$–$C_7$) hydrocarbon silyloxyl group, $C_2$–$C_7$ acyloxyl group, $C_2$–$C_5$ alkoxycarbonyloxyl group, $C_1$–$C_4$ alkoxyl group, $C_2$–$C_7$ acyl group, $C_2$–$C_5$ alkoxycarbonyl group, or $C_1$–$C_4$ alkyl group; or group where R$^{92}$ and R$^{920}$ bond with each other to form a 5- or 6-membered ring.

As preferable examples of the halogen atom of the substituent (i), mention may be made of a fluorine, chlorine, bromine, or iodine atom.

As examples of R$^{62}$ of the group having —COOR$^{62}$ of the substituent (v), mention may be made of a hydrogen atom; 1 equivalent of cations such as, ammonium, tetramethyl ammonium, cyclohexyl ammonium, benzyl ammonium, phenethyl ammonium, etc. or morpholinium cations, piperidinium cations or Na$^+$, K$^+$, ½Ca$^{2+}$, ½Mg$^{2+}$, ⅓Al$^{3+}$, residues of saccharides, for example, altrose, glucose, mannose, galactose, ribose, arabinose, xylose, fructose, and other monosaccharides or their deoxysugars; and $C_1$–$C_{10}$ aliphatic hydrocarbon groups such as a methyl, ethyl, propyl, isopropyl, butyl, s-butyl, t-butyl, pentyl, neopentyl, hexyl, octyl, or decyl group or other alkyl group, 2-propenyl, 2-butenyl, 2-hexenyl, or 5-hexenyl group or other alkenyl group, 2-butynyl, 3-hexynyl, or other alkynyl groups, which may be substituted with the substituents of a fluorine, chlorine, bromine, iodine, oxo group, hydroxyl group, trimethylsilyloxyl, triethylsilyloxyl, or t-butyldimethylsilyloxyl group or other tri ($C_1$–$C_7$) hydrocarbon silyloxyl groups, acetoxyl, propionyloxyl, butyryloxyl, isobutyryloxyl, valeryloxyl, or benzoyloxyl group or other $C_2$–$C_7$ acyloxyl groups, methoxycarbonyloxyl, ethoxycarbonyloxyl, propoxycarbonyloxyl, isopropoxycarbonyloxyl, or butoxycarbonyloxyl group or other $C_2$–$C_5$ alkoxycarbonyloxyl groups, methoxyl, ethoxyl, propoxyl, isopropoxyl, butoxyl, s-butoxyl, or t-butoxyl group or other $C_1$–$C_4$ alkoxyl groups, cyclobutyl, cyclopentyl, or cyclohexyl group or other $C_4$–$C_{10}$ alicyclic hydrocarbon groups, or phenyl, 1-naphthyl, or 2-naphthyl group or other $C_6$–$C_{10}$ aromatic hydrocarbon groups.

Examples of R$^{72}$ of the group OR$^{72}$ of the substituent (vi) are a hydrogen atom; methyl, ethyl, propyl, isopropyl, butyl, isobutyl, s-butyl, or t-butyl group or other $C_1$–$C_4$ alkyl groups; acetyl, propionyl, butyryl, isobutyryl, valeryl, isovaleryl, hexanoyl, heptanoyl, or benzoyl group or other $C_2$–$C_7$ acyl groups; methoxycarbonyl, ethoxycarbonyl, propoxycarbonyl, isopropoxycarbonyl, butoxycarbonyl, isobutoxycarbonyl, or t-butoxycarbonyl group or other $C_2$–$C_5$ alkoxycarbonyl groups; trimethylsilyl, triethylsilyl, t-butyldimethylsilyl, t-butyldiphenylsilyl, or tribenzylsilyl group or other tri ($C_1$–$C_7$) hydrocarbon silyl groups; methoxymethyl, 1-ethoxyethyl, 1-methoxy-1-methylethyl, 2-ethoxy-1-methylethyl, 2-methoxyethoxymethyl, tetrahydropyran-2-yl, or tetrahydrofuran-2-yl group or other groups forming an acetal bond with the oxygen atom to which $R^{72}$ is bonded; $C_1$–$C_{10}$ aliphatic hydrocarbon groups such as methyl, ethyl, propyl, isopropyl, butyl, isobutyl, s-butyl, t-butyl, pentyl, isopentyl, neopentyl, t-pentyl, hexyl, heptyl, octyl, nonyl, or decyl group or other alkyl groups, 2-propenyl, 2-butenyl, 3-butenyl, or 3-hexenyl group or other alkenyl groups, 2-propynyl, 2-butynyl, or 3-hexynyl group or other alkynyl groups, or $C_4$–$C_{10}$ alicyclic hydrocarbon groups such as cyclobutyl, heptyl, octyl, nonyl, or decyl group or other alkyl groups, 2-propenyl, 2-butenyl, 3-butenyl, or 3-hexenyl group or other alkenyl groups, 2-propynyl, 2-butynyl, or 3-hexynyl group or other alkynyl groups, or $C_4$–$C_{10}$ alicyclic hydrocarbon groups such as cyclobutyl, cyclopentyl, cyclohexyl, 3-cyclohexenyl, 4-cyclohexenyl, cyclooctyl, or bicyclo [4.4.0] decane-2-yl group which may be substituted with the substituents of fluorine, chlorine, bromine, iodine, oxo group, hydroxyl group, nitro group, carboxyl group, cyano group, trimethylsilyloxyl, triethylsilyloxyl, or t-butyldimethylsilyloxyl group or other tri ($C_1$–$C_7$) hydrocarbon silyloxyl groups, acetoxyl, propionyloxyl, butyryloxyl, isobutyryloxyl, valeryloxyl, hexanoyloxyl, or benzoyloxyl group or other $C_2$–$C_7$ acyloxyl groups, methoxycarbonyloxyl, ethoxycarbonyloxyl, propoxycarbonyloxyl, isopropoxycarbonyloxyl, butoxycarbonyloxyl, or t-butoxycarbonyloxyl group or other $C_2$–$C_5$ alkoxycarbonyoxyl groups, methoxyl, ethoxyl, propoxyl, isopropoxyl, butoxyl, isobutoxyl, s-butoxyl, or t-butoxyl group or other $C_1$–$C_4$ alkoxyl groups, acetyl, propionyl, butyryl, isobutyryl, valeryl, hexanoyl, heptanoyl, or benzoyl group or other $C_2$–$C_7$acyl groups, methoxycarbonyl, ethoxycarbonyl, propoxycarbonyl, isopropoxycarbonyl, butoxycarbonyl, isobutoxycarbonyl, or t-butoxycarbonyl group or other $C_2$–$C_5$ alkoxycarbonyl groups, phenyl, 1-napthyl, or 2-napthyl group or other $C_6$–$C_{10}$ aromatic hydrocarbon groups; or $C_6$–$C_{10}$ aromatic hydrocarbon groups such as phenyl, 1-napthyl, or 2-napthyl group, which may be substituted with the substituents of fluorine, chlorine, bromine, or iodine, hydroxyl group, nitro group, carboxyl group, cyano group, trimethylsilyloxyl, triethylsilyloxyl, or t-butyldimethylsilyloxyl group or other tri ($C_1$–$C_7$) hydrocarbon silyloxyl groups, acetoxyl, propionyloxyl, butyryloxyl, isobutyryloxyl, valeryloxyl, hexanoyloxyl, or benzoyloxyl group or other $C_2$–$C_7$ acyloxyl groups, methoxycarbonyloxyl, ethoxycarbonyloxyl, propoxycarbonyloxyl, isopropoxycarbonyloxyl, butoxycarbonyloxyl, or t-butoxycarbonyloxyl group or other $C_2$–$C_5$ alkoxycarbonyloxyl groups, methoxyl, ethoxyl, propoxyl, isopropoxyl, butoxyl, isobutoxyl, s-butoxyl, or t-butoxyl group or other $C_1$–$C_4$ alkoxyl groups, acetyl, propionyl, butyryl, isobutyryl, valeryl, hexanoyl, heptanoyl, or benzoyl group or other $C_2$–$C_7$ acyl groups, methoxycarbonyl, ethoxycarbonyl, propoxycarbonyl, isopropoxycarbonyl, butoxycarbonyl, isobutoxycarbonyl, or t-butoxycarbonyl group or other $C_2$–$C_5$ alkoxycarbonyl groups, or methyl, ethyl, propyl, isopropyl, butyl, isobutyl, s-butyl, t-butyl, or other $C_1$–$C_4$ alkyl group Examples of the $R^{82}$ and $R^{820}$ represented by —CONR$^{82}$R$^{820}$ of the substituent (vii), are a hydrogen atom; $C_1$–$C_{10}$ aliphatic hydrocarbon groups, such as a methyl, ethyl, propyl, isopropyl, butyl, isobutyl, s-butyl, t-butyl, pentyl, isopentyl, neopentyl, t-pentyl, hexyl, heptyl, octyl, nonyl, or decyl group or other alkyl groups, 2-propenyl, 2-butenyl, 2-penthenyl, or 3-hexenyl group or other alkenyl group, 2-propynyl, 2-butynyl, 2-pentynyl, or 3-hexynyl group or other alkynyl groups; $C_4$–$C_{10}$ alicyclic hydrocarbon groups such as cyclobutyl, cyclopentyl, cycloheptyl, cyclooctyl, or bicyclo [4.4.0] decane-2-yl group which may be substituted with the substituents of fluorine, chlorine, bromine, iodine, oxo group, hydroxyl group, nitro group, carboxyl group, trimethylsilyloxyl, triethylsilyloxyl, or t-butyldimethylsilyloxyl group or other tri ($C_1$–$C_7$) hydrocarbon silyloxyl groups, acetoxyl, propionyloxyl, butyryloxyl, isobutyryloxyl, valeryloxyl, hexanoyloxyl, or benzoyloxyl group or other $C_2$–$C_7$ acyloxyl groups, methoxycarbonyloxyl, ethoxycarbonyloxyl, propoxycarbonyloxyl, isopropoxycarbonyloxyl, butoxycarbonyloxyl, or t-butoxycarbonyloxyl group or other $C_2$–$C_5$ alkoxycarbonyloxyl groups, methoxyl, ethoxyl, propoxyl, isopropoxyl, butoxyl, isobutoxyl, s-butoxyl, or t-butoxyl group or other $C_1$–$C_4$ alkoxyl groups, acetyl, propionyl, butyryl, isobutyryl, valeryl, hexanoyl, heptanoyl, or benzoyl group or other $C_2$–$C_7$ acyl groups, methoxycarbonyl, ethoxycarbonyl, propoxycarbonyl, isopropoxycarbonyl, butoxycarbonyl, isobutoxycarbonyl, or t-butoxycarbonyl group or other $C_2$–$C_5$ alkoxycarbonyl groups; $C_6$–$C_{10}$ aromatic hydrocarbon groups such as phenyl, 1-napthyl, or 2-napthyl group; $C_6$–$C_{10}$ aromatic hydrocarbon group, such as a phenyl, 1-naphthyl, or 2-naphthyl group, which may be substituted with the substituents of fluorine, chlorine, bromine, iodine, hydroxyl group, nitro group, carboxyl group, cyano group, trimethylsilyloxyl, triethylsilyloxyl, or t-butyldimethylsilyloxyl group or other tri ($C_1$–$C_7$) hydrocarbon silyloxyl groups, acetoxyl, propionyloxyl, butyryloxyl, isobutyryloxyl, valeryloxyl, hexanoyloxyl, or benzoyloxyl group or other $C_2$–$C_7$ acyloxyl groups, methoxycarbonyloxyl, ethoxycarbonyloxyl, propoxycarbonyloxyl, isopropoxycarbonyloxyl, butoxycarbonyloxyl, t-butoxycarbonyloxyl, and other $C_2$–$C_5$ alkoxycarbonyloxyl groups, methoxyl, ethoxyl, propoxyl, isopropoxyl, butoxyl, isobutoxyl, s-butoxyl, t-butoxyl, and other $C_1$–$C_4$ alkoxyl groups, acetyl, propionyl, butyryl, isobutyryl, valeryl, hexanoyl, heptanoyl, or benzoyl group or other $C_2$–$C_7$ acyl groups, methoxycarbonyl, ethoxycarbonyl, propoxycarbonyl, isopropoxycarbonyl, butoxycarbonyl, isobutoxycarbonyl, or t-butoxycarbonyl group or other $C_2$–$C_5$ alkoxycarbonyl groups, methyl, ethyl, propyl, isopropyl, butyl, isobutyl, s-butyl, t-butyl, or other $C_1$–$C_4$ alkyl groups; or a group where $R^{82}$ and $R^{820}$ bond with each other to form a 5- or 6-membered ring together with the nitrogen atom sandwiched by the $R^{82}$ and $R^{820}$, for example, a 1-pyrrolidinyl, 1-piperidinyl, 1-imidazolidinyl, 1-piperidinyl, 4-morpholinyl, or 2-thioxo-3-thiazolinyl group, which may be substituted with the substituents of a methoxyl, ethoxyl, propoxyl, isopropoxyl, butoxyl, isobutoxyl, s-butoxyl, or t-butoxyl group or other $C_1$–$C_4$ alkoxyl groups, methyl, ethyl, propyl, isopropyl, butyl, isobutyl, s-butyl, or t-butyl group or other $C_1$–$C_4$ alkyl groups.

Examples of $R^{92}$ and $R^{920}$ represented by the NR$^{92}$R$^{920}$ of the substituent (viii) are a hydrogen atom; $C_1$–$C_{10}$ aliphatic hydrocarbon groups such as methyl, ethyl, propyl, isopropyl, butyl, isobutyl, s-butyl, t-butyl, pentyl, isopentyl, neopentyl, t-pentyl, hexyl, heptyl, octyl, nonyl, or decyl group or other alkyl groups, 2-propenyl, 2-butenyl, 2-penthenyl, 2-hexenyl, 5-hexenyl, and other alkenyl groups, 2-butynyl, 2-pentynyl, or 3-hexynyl group or other alkynyl groups; or cyclobutyl, cyclopentyl, cyclohexyl, cycloheptyl, cyclooctyl, or bicyclo [4.4.0] decane-2-yl group, or other $C_4$–$C_{10}$ alicyclic hydrocarbon groups; which may be substituted with the substituents of fluorine, chlorine, bromine, iodine, oxo group, hydroxyl group, nitro group, carboxyl group, trimethylsilyloxyl, triethylsilyloxyl, or t-butyldimethylsilyloxyl group or other tri ($C_1$–$C_7$) hydrocarbon silyloxyl groups, acetoxyl, propionyloxyl, butyryloxyl, isobutyryloxyl, valeryloxyl, hexanoyloxyl, or benzoyloxyl group or other $C_2$–$C_7$ acyloxyl groups, methoxycarbonyloxyl, ethoxycarbonyloxyl, propoxycarbonyloxyl, isopropoxycarbonyloxyl, butoxycarbonyloxyl, t-butoxycarbonyloxyl, or other $C_2$–$C_5$ alkoxycarbonyloxyl groups, methoxyl, ethoxyl, propoxyl, isopropoxyl, butoxyl, isobutoxyl, s-butoxyl, t-butoxyl, or other $C_1$–$C_4$ alkoxyl groups, acetyl, propionyl, butyryl, isobutyryl, valeryl, hexanoyl, heptanoyl, benzoyl, or other $C_2$–$C_7$ acyl groups, methoxycarbonyl, ethoxycarbonyl, propoxycarbonyl, isopropoxycarbonyl, butoxycarbonyl, isobutoxycarbonyl, or t-butoxycarbonyl group or other $C_2$–$C_5$ alkoxycarbonyl groups or phenyl, 1-napthyl, and 2-napthyl group or other, $C_6$–$C_{10}$ aromatic hydrocarbon groups such as phenyl, 1-napthyl, and 2-napthyl which may be substituted with the substituents of fluorine, chlorine, bromine, or iodine; hydroxyl group, nitro group, carboxyl group, cyano group, trimethylsilyloxyl, triethylsilyloxyl, or t-butyldimethylsilyloxyl group or other tri ($C_1$–$C_7$) hydrocarbon silyloxyl groups, acetoxyl, propionyloxyl, butyryloxyl, valeryloxyl, hexanoyloxyl, or benzoyloxyl group or other $C_2$–$C_7$ acyloxyl groups, methoxycarbonyloxyl, ethoxycarbonyloxyl, propoxycarbonyloxyl, isopropoxycarbonyloxyl, butoxycarbonyloxyl, t-butoxycarbonyloxyl, or other $C_2$–$C_5$ alkoxycarbonyloxyl groups, methoxyl, ethoxyl, propoxyl, isopropoxyl, butoxyl, isobutoxyl, s-butoxyl, or t-butoxyl group or other $C_1$–$C_4$ alkoxyl groups, acetyl, propionyl, butyryl, isobutyryl, valeryl, isovaleryl, hexanoyl, heptanoyl, or benzoyl group or other $C_2$–$C_7$ acyl groups, methoxycarbonyl, ethoxycarbonyl, propoxycarbonyl, isopropoxycarbonyl, butoxycarbonyl, isobutoxycarbonyl, or t-butoxycarbonyl group or other $C_2$–$C_5$ alkoxycarbonyl groups; methyl, ethyl, propyl, isopropyl, butyl, isobutyl, s-butyl, or t-butyl group or other $C_1$–$C_4$ alkyl groups; or a group where $R^{92}$ and $R^{920}$ bond with each other to form a 5-membered ring or 6-membered ring together with the nitrogen atom sandwiched by the $R^{92}$ and $R^{920}$, for example, 1-piperidinyl, 1-imidazolidinyl, 1-piperadinyl, 4-morpholinyl, and 2-thioxo-3-thiazolinyl group substitutable by the methoxyl, ethoxyl, propoxyl, isopropoxyl, butoxyl, isobutoxyl, s-butoxyl, or t-butoxyl group or other $C_1$–$C_4$ alkoxyl groups and the methyl, ethyl, propyl, isopropyl, butyl, isobutyl, s-butyl, or t-butyl group or other $C_1$–$C_4$ alkyl groups.

Preferable examples of $R^2$ are cyclobutyl, cyclopentyl, cyclohexyl, 1-cyclohexenyl, 3-cyclohexenyl, 4-cyclohexenyl, 4-methoxycyclohexenyl, cycloheptyl, cyclooctyl, phenyl, 4-methylphenyl, 4-dimethylaminophenyl, 4-methoxycarbonylphenyl, 4-benzyloxyphenyl, 4-(3-hydroxy-2-hyhydroxymethylpropyl)phenyl, 3-methoxyphenyl, 4-methoxyphenyl, 3,5-dichlorophenyl, 3,5-difluorophenyl, 4-iodophenyl, 4-nitrophenyl, 4-cyanophenyl, 3-trifluoromethyl, phenyl, 2-napthyl, vanyl, piperonyl, furyl, 5-methyl-2-furanyl, thienyl, 3-pyridinyl, 4-pyridinyl, 2-pyrrolyl, 2-oxazolyl, morphonilinyl, etc.

In the above-mentioned formula (I), $R^3$ represents a substituted or unsubstituted (i) $C_1$–$C_{10}$ aliphatic hydrocarbon group, (ii) $C_4$–$C_{10}$ alicyclic hydrocarbon group, (iii) $C_6$–$C_{10}$ aromatic hydrocarbon group, or (iv) hydrogen atom. A preferable group of $R^3$ may include a substituted or unsubstituted $C_1$–$C_{10}$ aliphatic hydrocarbon group.

The unsubstituted $C_1$–$C_{10}$ aliphatic hydrocarbon group of $R^3$ may include, for example, the methyl, ethyl, propyl, isopropyl, butyl, isobutyl, s-butyl, t-butyl, pentyl, isopentyl, neopentyl, hexyl, heptyl, octyl, 3,7- dimethyloctyl, nonyl, decyl, or other alkyl group; vinyl, 1-methylvinyl, 1-propenyl, 2-propenyl, 2-methyl-1-propenyl, 1-butenyl, 2-butenyl, 2-methyl-1-butenyl, 1-penthenyl, 2-penthenyl, 1-hexenyl, 2-hexenyl, 3,3-dimethyl-1-butenyl, 5-hexenyl, 1,5-hexadienyl, 1-heptenyl, 1-octenyl, 3-methyl-1-octenyl, 4,4-dimethyl-1-octenyl, 1,7-octadienyl, 1-nonenyl, 5-methyl-1-nonenyl or 1-decenyl group or other alkenyl group; ethynyl, 1-propynyl, 2-propynyl, 1-butynyl, 3-methyl-1-butynyl, 3, 3-dimethyl-1-butynyl, 1-pentynyl, 2-pentynyl, 1-hexynyl, 2-hexynyl, 5-hexene-1-ynyl, 1-heptynyl, 1-nonynyl or 1-decynyl group or other alkynyl group.

Examples of the unsubstituted $C_4$–$C_{10}$ alicyclic hydrocarbon group of $R^3$ are cyclobutyl, cyclopentyl, cyclohexyl, 1-cyclohexenyl, 3-cyclohexenyl, 4-cyclohexenyl, cycloheptyl, cyclooctyl, or bicyclo [4.4.0] decane-2-il group or other monocyclic or bicyclic groups.

Examples of the unsubstituted $C_6$–$C_{10}$ aromatic hydrocarbon group of $R^3$ are phenyl, 1-napthyl, and 2-napthyl groups.

When $R^3$ represents a (i) $C_1$–$C_{10}$ aliphatic hydrocarbon group, (ii) $C_4$–$C_{10}$ alicyclic hydrocarbon group, or (iii) $C_6$–$C_{10}$ aromatic hydrocarbon group having a substituent, the following (i) to (viii) may be mentioned as the substituent.

(i) halogen atom
(ii) oxo group
(iii) cyano group
(iv) nitro group
(v) —$COOR^{63}$ wherein $R^{63}$ is the same as $R^{62}$
(vi) —$OR^{73}$ wherein $R^{73}$ is the same as $R^{72}$
(vii) —$CONR^{83}R^{830}$ wherein $R^{83}$ and $R^{830}$ are the same or different and are the same as $R^{82}$ and $R^{820}$
(viii) —$NR^{93}R^{930}$ wherein $R^{93}$ and $R^{930}$ are the same or and are the same as $R^{92}$ and $R^{920}$ Examples of the above substituent are those in the examples of substituents $R^2$ mentioned above.

Examples of the substituent $R^3$ are a hydrogen atom, methyl, ethyl, propyl, isopropyl, butyl, t-butyl, octyl, 3,7-dimethyloctyl, 3,7-dimethyl-6-octenyl, 1-methylvinyl, 1-octenyl, 3,3 -dimethyl-4-phenyl-1-butenyl, 3,3-dimethyl-1-butynyl, 1-pentynyl, 1-hexynyl, 3-t-butyldimethylsilyloxy-1-octenyl, 3-hydroxy-1-octenyl, 3-acetoxy-1-octenyl, 3-methoxycarbonyloxy-1-octenyl, 3-trimethylsilyloxy-3-methyl-1-octenyl, 3-hydroxy-3-methyl-1-octenyl, 3-t-butyldimethylsilyloxy-5-methyl-1-nonenyl, 3-hydroxy-5-methyl-1-nonenyl, 6-carboxyhexyl, 6-methoxycarbonylhexyl, 6-(2-thioxo-3-thiazolidinylcarbonyl)hexyl, 6-(6-D-glucosylcarbonyl) hexyl, 6-(1-D-xylosylcarbonyl)hexyl, 6-(5-D-ribosylcarbonyl)hexyl, 6-hydroxyhexyl, 6-t-butyldimethylsilyloxyhexyl, 6-acetoxyhexyl, 6-hydroxy-2- hexenyl, 6-carboxy-2-hexenyl, 6-methoxycarbonyl-2-hexenyl, 3-cyclohexylpropyl, 3-hydroxy-3-cyclopentyl-1-propenyl, 3-methoxycarbonyloxy-3-cyclopentyl-1-propenyl, 3-isopropoxycarbonyloxy-3-cyclopentyl-1-propenyl, 3-t-butyldimethylsilyloxy-3-cyclopentyl-1-propenyl, 3-hydroxy-3-cyclohexyl-1-propenyl, 3-t-butyldimethylsilyloxy-3-cyclohexyl-1-propenyl, 3-hydroxy-4-cyclohexyl-1-butenyl, 4-phenoxybutyl, 4-(2,4, 6-triiodophenoxy)butyl, 3-(3,4-dimethoxyphenyl)propyl, benzil, 2-phenylethyl, 5-phenylpentyl, cyclohexyl, and phenyl.

In formula (I), $R^4$ is a hydrogen atom, $C_1$–$C_4$ alkyl group, $C_2$–$C_7$ acyl group, $C_2$–$C_5$ alkoxycarbonyl group, tri ($C_1$–$C_7$) hydrocarbon silyl group, or group forming an acetal bond with the oxygen atom to which $R^4$ is bonded.

Examples of the $C_1$–$C_4$ alkyl group of $R^4$ are a methyl, ethyl, propyl, isopropyl, butyl, isobutyl, s-butyl, or t-butyl group. Examples of $C_2$–$C_7$ of acyl group are acetyl, propionyl, butyryl, isobutyryl, valeryl, isovaleryl, hexanoyl, heptanoyl, or benzoyl group. Examples of $C_2$–$C_5$ alkoxycarbonyl group are methoxycarbonyl, ethoxycarbonyl, propoxycarbonyl, isopropoxycarbonyl, butoxycarbonyl, isobutoxycarbonyl, and t-butoxycarbonyl group. Examples of the tri ($C_1$–$C_7$) hydrocarbon silyl group are trimethylsilyl, triethylsilyl, t-butyldimethylsilyl, t-butyldiphenylsilyl, and tribenzylsilyl group. Examples of the group forming an acetal bond with the oxygen atom to which $R^4$ is bonded are methoxymethyl, 1-ethoxyethyl, 1-methoxy-1-methylethyl, 2-ethoxy-1-methylethyl, 2-methoxyethoxymethyl, tetrahydropyran-2-yl, tetrahydrofuran-2-yl, 6,6-dimethyl-3-oxa-2-oxo-bicyclo [3.1.0] hexane-4-yl group.

As $R^4$, a hydrogen atom or tri ($C_1$–$C_7$) hydrocarbon silyl group is preferable, in particular, a hydrogen atom or trimethylsilyl group is preferable.

In the above-mentioned formula (I), $R^5$ represents a substituted or unsubstituted (i) $C_1$–$C_{10}$ aliphatic hydrocarbon group, (ii) $C_4$–$C_{10}$ alicyclic hydrocarbon group, or (iii) hydrogen atom.

The preferable group of $R^5$ is a substituted or unsubstituted $C_1$–$C_{10}$ aliphatic hydrocarbon group or a hydrogen atom. In particular, a hydrogen atom is preferable.

Examples of the unsubstituted $C_1$–$C_{10}$ aliphatic hydrocarbon group of $R^5$ are methyl, ethyl, propyl, isopropyl, butyl, isobutyl, s-butyl, t-butyl, pentyl, isopentyl, neopentyl, hexyl, heptyl, octyl, 3,7-dimethyloctyl, nonyl, or decyl group or other alkyl groups; 2-propenyl, 2-butenyl, 3-butenyl, or 3-hexenyl group or other alkenyl groups; 2-propynyl or 2-butynyl group or other alkynyl groups, etc.

Examples of the unsubstituted $C_4$–$C_{10}$ alicyclic hydrocarbon group of $R^5$ are cyclobutyl, cyclopentyl, cyclohexyl, 3-cyclohexenyl, cyclooctyl, or bicyclo [4.4.0] decane-2-yl group or other monocyclic and bicyclic groups.

When $R^5$ represents a (i) $C_1$–$C_{10}$ aliphatic hydrocarbon group or a (ii) $C_4$–$C_{10}$ alicyclic hydrocarbon group having a substituent, mention may be made of the following (i) to (viii) as the substituent:

(i) halogen atom (ii) oxo group (iii) cyano group (iv) nitro group (v) —$COOR^{65}$ wherein $R^{65}$ is the same as $R^{62}$ (vi) —$OR^{75}$ wherein $R^{75}$ is the same as $R^{72}$ (vii) —$CONR^{85}R^{850}$ wherein $R^{85}$ and $R^{850}$ are the same or different and are the same as $R^{82}$ and $R^{820}$ (viii) —$NR^{95}R^{950}$ wherein $R^{95}$ and $R^{950}$ are the same or different and are the same as $R^{92}$ and $R^{920}$ Examples of the substituents are same as those of the substituents of $R^2$ mentioned above.

Preferable examples of $R^5$ are a hydrogen atom, methyl, ethyl, propyl, isopropyl, butyl, isobutyl, s- butyl, t-butyl, hexyl, octyl, 3,7-dimethyloctyl, 3,7-dimethyl-6-octenyl, benzyl, 3-(3,4-dimethoxyphenyl)propyl, 5-phenylpentyl, cyclohexyl, 3-cyclohexylpropyl, 4-cyclohexylbutyl, 6-hydroxyhexyl, 6-t-butyldimethylsilyloxyhexyl, 6-acetoxyhexyl, 6-(1-ethoxyethoxy)hexyl, 6-carboxyhexyl, 6-methoxycarbonylhexyl, 6-(6-D-glucosylcarbonyl)hexyl, 4-phenoxybutyl, etc. In particular, a hydrogen atom or methyl group is preferred.

Among the optically active 4-hydroxy-2-cyclopentenone derivatives of the above-mentioned formula (I) and mixtures thereof, the starting 4-hydroxy-2-cyclopentenone derivative having the formula (I-2-2) in accordance with the following scheme 1:

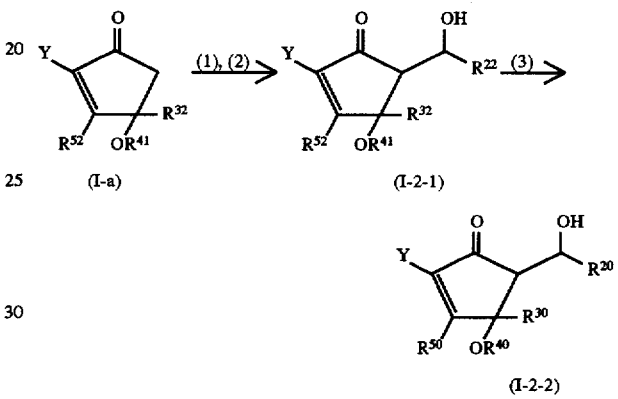

(1) Lithium amides or (tertiary amines and dialkyl borotrifluoromethanesulfonic acid)

(2) OHC—$R^{22}$ (II)

(3) Deblocking reaction of protecting group of hydroxyl group, protecting reaction of hydroxyl group, hydrolysis reaction of ester, esterification reaction of carboxyl group, amidation reaction, condensation reaction of sugar residue, salt forming reaction In the formulae in the scheme 1 above, $R^{20}$ and $R^{22}$ represent a substituted or unsubstituted $C_4$–$C_{10}$ alicyclic hydrocarbon group, $C_6$–$C_{10}$ aromatic hydrocarbon group or $C_1$–$C_9$ heterocyclic group, $R^{30}$ and $R^{32}$ are a hydrogen atom, substituted or unsubstituted $C_1$–$C_{10}$ aliphatic hydrocarbon group, $C_4$–$C_{10}$ alicyclic hydrocarbon group, or $C_6$–$C_{10}$ aromatic hydrocarbon group, $R^{40}$ and $R^{41}$ are a $C_1$–$C_4$ alkyl group, $C_2$–$C_7$ acyl group, $C_2$–$C_5$ alkoxycarbonyl group, tri ($C_1$–$C_7$) hydrocarbon silyl group, or a group forming an acetal bond together acid) to obtain the 4-hydroxy-2-cyclopentenone derivative having the formula (I-2-1), then, if desired, applying a deblocking reaction of the protective group of the hydroxyl group; the blocking reaction of the hydroxyl group; hydrolysis of the ester; esterification reaction of the carboxyl group; amidation reaction; condensation reaction of the sugar residue; and/or salt formation reaction.

The starting 4-hydroxy-2-cyclopentenone derivative having the above-mentioned formula (I-a) is produced in the same way as the method described, for example, in European Published Application No. 180399 or Japanese Unexamined Patent Publication (Kokai) No. 63-72672.

Among the 4-hydroxy-2-cyclopentenone derivatives of the above-mentioned formula (I) according to the present invention, the 4-hydroxy-2-cyclopentenone derivative expressed by the formula (I-2-4) in accordance with the following scheme 2:

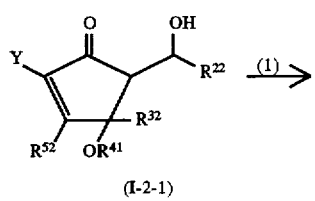

(I-2-1)

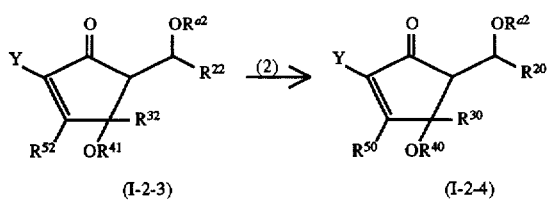

(I-2-3)     (I-2-4)

(1) Acylation reaction or alkoxycarbonylization reaction (2) Deblocking reaction of protecting group of hydroxyl group, protecting reaction of hydroxyl group, hydrolysis reaction of ester, esterification reaction of carboxyl group, amidation reaction, condensation reaction of sugar residue, salt forming reaction In the formulas in the scheme 2, $R^{20}$, $R^{22}$, $R^{30}$, $R^{32}$, $R^{40}$, $R^{41}$, $R^{50}$ and $R^{52}$ are the same as defined above. $R^{a1}$ represents a $C_2$–$C_7$ acyl group or $C_2$–$C_5$ alkoxycarbonyl group, and specific examples of $R^{a1}$ are those corresponding to the specific examples of the $C_2$–$C_7$ acyloxyl groups and $C_2$–$C_5$ alkoxycarbonyloxyl groups, in the form of —O—$R^{a1}$, mentioned in A for the above formula (I) can be produced by subjecting the 4-hydroxy-2-cyclopentenone derivative having the formula (I-2-1) to an acylation reaction or an alkoxycarbonylization reaction to obtain the 4-hydroxy-2-cyclopentenone derivative having the formula (I-2-3) then, if desired, applying a deblocking reaction of the protecting group of the hydroxyl group, a protecting reaction of the hydroxyl group, a hydrolysis reaction of the ester, an esterification reaction of the carboxyl group, an amidation reaction, a condensation reaction of the sugar residue and/or a salt forming reaction. Among the 4-hydroxy-2-cyclopentenones of the above-mentioned formula (I), the following scheme 3:

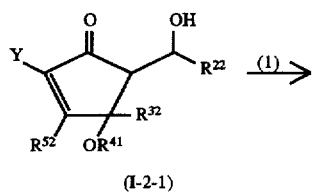

(I-2-1)

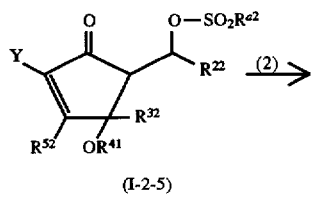

(I-2-5)

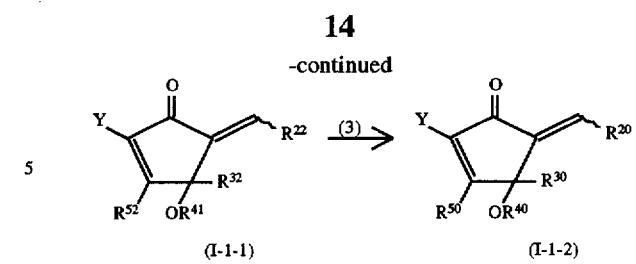

(I-1-1)     (I-1-2)

(1) Sulfonylization reaction
(2) Desulfonatization
(3) Deblocking reaction of protecting group of hydroxyl group, protecting reaction of hydroxyl group, hydrolysis reaction of ester, esterification reaction of carboxyl group, amidation reaction, condensation reaction of sugar residue, salt forming reaction wherein in the formulas in the scheme 3, $R^{20}$, $R^{22}$, $R^{30}$, $R^{32}$, $R^{40}$, $R^{41}$, $R^{50}$ and $R^{52}$ are the same as defined above, the wavy line ⁓ indicates the substituent bonded to the double bond is an E-configuration or Z-configuration or a mixture thereof in any ratio. $R^{a2}$ is a $C_1$–$C_4$ alkyl group substitutable by a halogen atom, a substituted or unsubstituted phenyl group, or a substituted or unsubstituted phenyl ($C_1$–$C_2$) alkyl group, and, specific examples of $R^{a2}$ are those corresponding to the specific examples of the $C_1$–$C_4$ alkylsulfonyloxyl group, which may be substituted with a halogen atom, substituted or unsubstituted phenylsulfonyloxyl group, or substituted or unsubstituted phenyl ($C_1$–$C_2$) alkylsulfonyloxy group as mentioned previously for A in the above-mentioned formula (I) in the form of —O—$SO_2R^{a2}$ may be produced by subjecting the 4-hydroxy-2-cyclopentenone derivative having the formula (I-2-1) to a sulfonylization reaction to obtain the 4-hydroxy-2-cyclopentenone derivative having the formula (I-2-5), then causing desulfonation to obtain the 4-hydroxy-2-cyclopentenone derivative having the formula (I-1-1), then, if desired, applying a deblocking reaction of the protective group of the hydroxyl group, a blocking reaction of the hydroxyl group, a hydrolysis reaction of the ester, an esterification reaction of the carboxyl group, an amidation reaction, a condensation reaction of the sugar residue, and/or a salt formation reaction.

Among the 4-hydroxy-2-cyclopentenone derivatives and mixtures of the above-mentioned formula (I-1) according to the present invention, the 4-hydroxy-2-cyclopentenone derivatives and mixtures having the formula (I-1-2) in accordance with the following scheme 4:

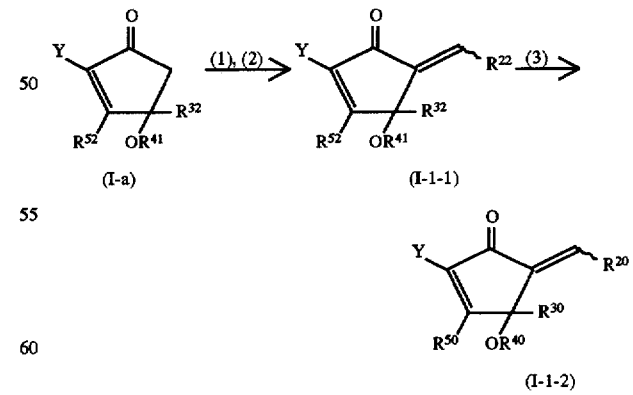

(I-a)     (I-1-1)

(I-1-2)

(1) Zirconium tetra-t-butoxide
(2) OHC—$R^{22}$ (II) Deblocking reaction of protecting group of hydroxyl group, protecting reaction of hydroxyl group, hydrolysis reaction of ester, esterification reaction of carboxyl group, amidation reaction, condensation reaction of sugar residue, salt forming reaction In the formulas in the scheme 4, $R^{10}$, $R^{12}$, $R^{20}$, $R^{22}$, $R^{30}$, $R^{32}$, $R^{40}$, $R^{41}$, $R^{12}$, $R^{50}$, and $R^{52}$ and the wavy line ⌇ are the same as defined above may he produced by subjecting the 4-hydroxy-2-cyclopentenone derivatives and mixtures having the formula (I-a) to an aldehyde condensation reaction with the aldehydes having the formula (II) using zirconium tetra-t-butoxide to obtain the 4-hydroxy-2-cyclopentenone derivatives and mixtures thereof having the formula (I-1-1), then, if desired, applying a deblocking reaction of the protecting group of the hydroxyl group, a protecting reaction of the hydroxyl group, a hydrolysis reaction of the ester an esterification reaction of the carboxyl group, an amidation reaction, a condensation reaction of the sugar residue, and/or a salt forming reaction.

The compounds of the present invention are administered to patients by methods such as oral administration, suppository administration, dermal administration, nasal administration, subcutaneous administration, intramuscular administration, intravenous injection and intra-arterial injection.

In the case of the oral administration, the compounds of the present invention may be in the form of a solid preparation or a liquid preparation. Examples of the dosage form include tablets, pills, powders, granules, solutions, suspensions and capsules.

Pharmaceutical preparations in the forth of a tablet are prepared by a conventional procedure through the use of additives, for example, excipients such as lactose, starch, calcium carbonate, crystalline cellulose and silicic acid; binders such as carboxymethyl cellulose, methyl cellulose, calcium phosphate and polyvinyl pyrrolidone; disintegrators such as sodium alginate, sodium bicarbonate, sodium laurylsulfate and monoglyceride stearate; lubricants such as glycerin; absorbers such as kaolin and colloidal silica; and lubricants such as talc and granular boric acid.

Pharmaceutical preparations in the form of a pill, powder or granule also may be prepared by a conventional procedure through the use of the same additives as those described above.

Liquid preparations, such as a solution and a suspension, also may be prepared by a conventional procedure. Examples of the carrier used include glycerol esters such as tricaprylin, triacetin and iodided poppy seed oil fatty acid esters; water; alcohols such as ethanol; and oleaginous bases such as liquid paraffin, coconut oil, soybean oil, sesame oil and corn oil.

The above-described powders, granules and liquid preparations may be encapsulated in a gelatin or the like.

In the present invention, the pharmaceutically acceptable carrier includes, besides the above-described carriers, auxiliary substances, perfuming agents, stabilizers and preservatures commonly used in the art, according to need.

Examples of the dosage form in the case of the dermal administration include ointments, creams, lotions and solutions.

Examples of the base for the ointment include fatty oils such as castor oil, olive oil, sesame oil and safflower oil, lanolin; white, yellow or hydrophilic petrolatum; wax; higher alcohols such as oleyl alcohol, isostearyl alcohol, octyldodecanol and hexyldecanol; and glycols such as glycerin, diglycerin, ethylene glycol, propylene glycol, sorbitol and 1,3-butanediol. Ethanol, dimethylsulfoxide, polyethylene glycol, etc. may be used as a solubilizing agent for the compound of the present invention. If necessary, it is also possible to use preservatives such as p-oxybenzoates, sodium benzoate, salicylic acid, sorbic acid and boric acid; and antioxidants such as butylhydroxyanisole and dibutylhydroxytoluene.

Absorbefacients, such as diisopropyl adipate, diethyl sebacate, ethyl caproate and ethyl laurate, may be added to thereby promote the percutaneous absorption. Further, to enhance the stabilization, the compounds of the present invention can be used in the form of a compound included in an α, β or γ-cyclodextrin.

The ointment can be prepared by a conventional procedure. The cream is preferably in an oil-in-water cream foden from the viewpoint of stabilizing the compounds of the present invention. The above-described fatty oils, higher alcohols and glycols are used as the base, and use is made of emulsifiers such as diethylene glycol, propylene glycol, sorbitan monofatty acid ester, polysorbate 80 and sodium laurylsulfate. Further, if necessary, the above-described preservatives, antioxidants, etc. may be added. As with the ointment, in the case of the cream, the compound of the present invention may be used in the form of a compound included in a cyclodextrin or a methylated cyclodextrin. The cream can be prepared by a conventional procedure.

Examples of the lotion include lotions in the form of a suspension, an emulsion and a solution. The lotion in the form of a suspension is prepared through the use of a suspending agent, such as sodium arginate, tragacanth or sodium carboxymethylcellulose, and antioxidants, preservatives, etc. are added thereto according to need.

The lotion in the form of an emulsion is prepared through the use of an emulsifier, such as sorbitan monofatty acid ester, polysorbate 80 or sodium laurylsulfate, by a conventional procedure.

The lotion in the form of a solution is preferably an alcoholic lotion, and the alcoholic lotion is prepared through the use of an alcohol, such as ethanol, by a conventional procedure. Examples of the preparation in the form of a solution include that prepared by dissolving the compound of the present invention in ethanol, and optionally, adding an antioxidant or a preservative, etc. to the solution.

Examples of other dosage forms include dermatologic pastes, cataplasms and aerosols. These preparations can be prepared by a conventional procedure.

The preparation for nasal administration is provided in the form of a liquid or powdery composition. Water, a saline solution, a phosphate buffer and an acetate buffer are used as a base for the liquid formulation, and the liquid formulation may contain surfactants, antioxidants, stabilizers, preservatives, and tackifiers. Water absorbing bases are preferred as a base for the powder formulation, and examples thereof include bases easily soluble in water, for example, polyacrylates such as sodium polyacrylate, potassium polyacrylate and ammonium polyacrylate, cellulose lower alkyl ethers, such as methyl cellulose, hydroxyethyl cellulose, hydroxypropyl cellulose and sodium carboxymethyl cellulose, polyethylene glycol polyvinyl pyrrolidone, amylose and pullulan, and bases hardly soluble in water, for example, celluloses such as crystalline cellulose, α-cellulose and crosslinked carboxymethyl cellulose, starches such as hydroxypropyl starch, carboxymethyl starch, crosslinked starch, amylose, amylopectin and pectin, proteins such as gelatin, casein, sodium casein, gums such as gum arabic, tragacanth gum and glucomannan, and crosslinked vinyl polymers such as polyvinyl polypyrrolidone, crosslinked polyacrylic acid and its salts, crosslinked polyvinyl alcohol and polyhydroxyethyl methacrylate, which may be used in the form of a mixture thereof. Further, the powder formulation may contain antioxidants, colorants, preservatives, antiseptics, and corrigents, etc. The above-described liquid and powder formulations may be administered by, for example, a spray.

The preparation for injection administration is provided in the form of an aseptic aqueous or non-aqueous solution, suspension on emulsion. In the non-aqueous solution or suspension, propylene glycol, polyethylene glycol, vegetable oils such as olive oil and injectable organic esters such as ethyl oleate and iodided poppy seed oil fatty acid ester are used as a pharmaceutically acceptable carrier. These preparations may contain auxiliary agents such as antiseptics, wetting agents, emulsifiers, dispersants and stabilizers, and may be in a sustained release forth. The above-described solutions, suspensions and emulsions can be made aseptic through a proper filtration whereby they are passed through a bacteria retaining filter, incorporation of a germicide, or treatments such as irradiation. Further, an aseptic solid preparation may be prepared and dissolved in an aseptic water or an aseptic solvent for injection immediately before use.

Further, it is also possible to use the compound of the present invention in the form of a compound included in an α, β or γ-cyclodextrin or a methylated cyclodextrin. Further, the compound of the present invention may be used in the form of an injection wherein a fat is bonded to the compound.

Although the effective dose of the compound of the present invention varies depending upon the administration method, age, sex and condition of patients, it is generally 1 to $10^5$ μg/kg/day, preferably about 10 to $10^4$ μg/kg/day.

EXAMPLES

The present invention will now be explained in further detail with reference to the following Examples, but by no means is not limited to these Examples.

Example 1

A 1.0 g amount of a starting (dl)-4-hydroxy-2-cyclopentenone derivative as shown in Table 1 below was dissolved in tetrahydrofuran and the resultant solution was added to a tetrahydrofuran solution of 4.13 mmol of lithium diisopropylamide in a nitrogen atmosphere at −78° C. The mixture was agitated for 15 minutes, then was added to a tetrahydrofuran solution of 430 mg of cyclohexanecarboaldehyde. After agitating for 2 hours, an aqueous ammonium chloride solution was added to stop the reaction and the extraction was performed by ethyl acetate. The organic layers were combined and then washed by a saturated saline solution and dried over magnesium sulfate. The resultant mixture was then filtered, concentrated, then subjected to silica gel column chromatography to obtain the (dl)-4-hydroxy-2-cyclopentenone derivative as shown in Table 1.

Example 2

A 200 mg amount of a starting (dl)-4-hydroxy-2-cyclopentenone derivative as shown in Table 1 below was taken, 2.5 mg of ether and 2.5 ml of hexane were added, then 160 μl of diisopropylethylamine were added and the mixture was cooled to −70° C. 750 μl of a 1M dichloromethane solution of dibutylborotrifluoromethane sulfonic acid was added and the resultant mixture was agitated for one hour. A solution of 160 mg of aldehyde in 10 ml of ether was cooled to −70° C. and added, then was agitated at −70° to −30° C. for 4 hours. An aqueous of ammonium chloride solution was added to stop the reaction and extraction was performed by ethyl acetate. The organic layers were combined and then washed by saturated saline solution. The result was then dried over magnesium sulfate, filtered, concentrated, then subjected to silica gel column chromatography to obtain the (dl)-4-hydroxy-2-cyclopentenone derivative as shown in Table 1.

Example 3

A 1.0 g amount of a starting (dl)-4-hydroxy-2-cyclopentenone derivative as shown in Table 1 below was dissolved in tetrahydrofuran. To this was added a tetrahydrofuran solution of 3.0 g of tetra-tert-butoxyzirconium in a nitrogen atmosphere at 0° C. The mixture was heated to room temperature, agitated for 20 minutes, then a tetrahydrofuran solution of 470 mg of 4-dimethylaminobenzaldehyde was added. After agitating for 20 hours, the reaction mixture was poured into ice water and extracted by ethyl acetate. The organic layers were combined, washed by saline solution, and dried over magnesium sulfate. The resultant product was filtered, concentrated, then subjected to silica gel column chromatography to obtain the (dl)-4-hydroxy-2-cyclopentenone derivative as shown in Table 1.

Examples 4 to 33

The same procedure was followed as in Example 3 to obtain the (dl)-4-hydroxy-2-cyclopentenone derivatives as shown in Table 1 below. In Examples 6 and 7, however, optically active starting materials were used as shown in Table 1 to obtain optically active 4-hydroxy-2-cyclopentenone derivatives.

Example 34

A 70 mg amount of methanesulfonyl chloride were added to a pyridine solution of 215 mg of a starting (dl)-4-hydroxy-2-cyclopentenone derivative as shown in Table 2 below at 0° C. and the resultant mixture was agitated at room temperature for 17 hours. Ice water was added, extraction performed with methylene chloride, then the combined organic layer was washed by saline solution and dried over magnesium sulfate. The resultant product was filtered, concentrated, then subjected to silica gel column chromatography to obtain the (dl)-4-hydroxy-2-cyclopentenone derivative as shown in Table 2.

Example 35

A 350 mg amount of 1,8-diazabicyclo [5.4.0]-7-undecene was added to a methylene chloride solution of 102 mg of a starting (dl)-4-hydroxy-2-cyclopentenone derivative as shown in Table 2 below and the mixture agitated at room temperature for 6 hours. The solvent was evaporated, then the resultant product was subjected to silica gel column chromatography to obtain the (dl)-4-hydroxy-2-cyclopentenone derivative as shown in Table 2.

Example 36

4-dimethylaminopyridine (1.5 g) was added to a dicyclomethane (30 ml) solution of 3.5 g of a starting (dl)-4-hydroxy-2-cyclopentenone derivative as shown in Table 3 below and the resultant mixture was cooled to 0° C. A 0.6 ml amount of methanesulfonyl chloride was dropwise added and the resultant mixture was agitated at room temperature for 13 hours. To this reaction mixture were added ethyl acetate and an aqueous potassium hydrogensulfate solution, the product was extracted to the organic layer, the extract was washed with an aqueous of sodium hydrogencarbonate solution and saline solution, the resultant product was dried over magnesium sulfate, then was filtered and concentrated. The resultant product was subjected to silica gel chromatography to obtain the (dl)-4-hydroxy-2-cyclopentenone derivative as shown in Table 3.

Example 37

A 0.3 ml amount of hydrogen fluoride pyridinium salt was added to a mixed solution of 0.6 ml of pyridine and 1.7 ml of acetonitrile at 0° C. To this was added an acetonitrile solution of 81 mg of a starting (dl)-4-hydroxy-2-cyclopentenone derivative as shown in Table 3 below. The mixture was heated to room temperature, then was agitated for 4 hours and was poured into an ice-cooled saturated aqueous sodium hydrogencarbonate solution. This was extracted by ethyl acetate, then the organic layers were combined and the resultant product was washed by saline solution and dried over magnesium sulfate. This was then filtered, concentrated, then subjected to silica gel column chromatography to obtain the (dl)-4-hydroxy-2-cyclopentenone derivative as shown in Table 3.

Examples 38 to 70

The same procedure was followed as in Example 37 to obtain the (dl)-4-hydroxy-2-cyclopentenone derivatives as shown in Table 3 below. However, Examples 41 and 42 used starting materials optically active to obtain optically active 4-hydroxy-2-cyclopentenone derivatives.

Example 71

A 60 mg amount of a starting (dl)-4-hydroxy-2-cyclopentenone derivative as shown in Table 4 were dissolved in 3 ml of dichloromethane and 200 µl of pyridine were added. 100 µl of acetylchloride was added and the resultant mixture was agitated for 12 hours. The resultant product was poured over an aqueous solution of potassium hydrogensulfate and extracted by ethyl acetate. The organic layer was washed by an aqueous sodium hydrogencarbonate solution and saline solution and dried over magnesium sulfate. The resultant product was filtered, concentrated, then subjected to silica gel chromatography to obtain the (dl)-4-hydroxy-2-cyclopentenone derivative as shown in Table 4.

Examples 72 to 73

The same procedure was followed as in Example 71 to obtain the (dl)-4-hydroxy-2-cyclopentenone derivatives as shown in Table 4 below.

Example 74

A 60 mg amount of a starting (dl)-4-hydroxy-2-cyclopentenone derivative as shown in Table 4 below was dissolved in 3 ml of dichloromethane and 500 µl of pyridine were added. 300 µl of methoxycarbonylchloride was added and the resultant mixture was agitated for 16 hours. The mixture was then poured over an aqueous potassium hydrogensulfate solution and extracted by ethyl acetate. The organic layer were combined, washed by an aqueous sodium hydrogencarbonate solution and saline solution, and dried over magnesium sulfate. The resultant product was then filtered, concentrated, then subjected to silica gel chromatography to obtain the (dl)-4-hydroxy-2-cyclopentenone derivative as shown in Table 4.

Example 75

A 80 mg of a starting (dl)-4-hydroxy-2-cyclopentenone derivative as shown in Table 4 below was dissolved in 5 ml of dichloromethane and 500 µl of pyridine was added thereto. 300 µl of benzoyl chloride was added and the mixture was agitated for 16 hours. This was poured over an aqueous potassium hydrogensulfate solution and the resultant mixture was extracted with ethyl acetate. The organic layers were combined, washed with an aqueous sodium hydrogencarbonate solution and saline solution, and dried over magnesium sulfate. The resultant product was then filtered and concentrated, then subjected to silica gel chromatography to obtain the (dl)-4-hydroxy-2-cyclopentenone derivative as shown in Table 4.

Example 76

A 500 mg amount of a starting (dl)-4-hydroxy-2-cyclopentenone derivative as shown in Table 4 below was dissolved in 20 ml of acetone and 220 ml of 0.1M phosphate buffer of pH 8 were added. 24 mg of pig liver esterase were added thereto, while agitating and the resultant mixture was agitated a 30° to 35° C. for 6 days. A 0.1N hydrochloric acid was added to adjust the pH 4, then ammonium sulfate was added to saturation, ethyl acetate was added, then filtration was performed. The filtrate was extracted over ethyl acetate and the organic layers were combined. The resultant mixture was washed with saline solution. The product was then dried over magnesium sulfate, filtered, and concentrated, then was subjected to silica gel chromatography to obtain the (dl)-4-hydroxy-2-cyclopentenone derivative as shown in Table 4.

Example 77

The same procedure was followed as in Example 76 to obtain the (dl)-4-hydroxy-2-cyclopentenone derivative as shown in Table 4 below.

Example 78

A 320 mg of a starting (dl)-4-hydroxy-2-cyclopentenone derivative as shown in Table 4 below was dissolved in 25 ml of dichloromethane and 120 µl of triethylamine were added thereto. The mixture was cooled to −20° C., 110 µl of pivaroyl chloride were added, and the mixture was agitated for 2 hours. Then, 95 mg of 2-mercaptothiazoline and 9 mg of 4-dimethylaminopyridine were added thereto and the mixture was agitated for 2 hours. An aqueous sodium hydrogencarbonate solution was added and extraction was performed with dichloromethane. The organic layer was washed with an aqueous solution of potassium hydrogensulfate, an aqueous solution of sodium hydrogencarbonate, and a saline solution and was dried over magnesium sulfate. The resultant product was filtered and concentrated, then was subjected to silica gel chromatography to obtain the (dl)-4-hydroxy-2-cyclopentenone derivative as shown in Table 4.

Example 79

A 85 mg amount of a starting (dl)-4-hydroxy-2-cyclopentenone derivative as shown in Table 4 below was dissolved in 4 ml of pyridine and 85 mg of D-glucose was added thereto. 3 mg of sodium hydride (60% in oil) and 3 mg of 4-dimethylaminopyridine were added and the resultant mixture was agitated for 16 hours. 5 ml of a 0.1M phosphate buffer of pH 7 was added and the resultant mixture was extracted with butanol. The organic layer was washed in a saline solution, concentrated, and subjected to silica gel chromatography to obtain the (dl)-4-hydroxy-2-cyclopentenone derivative shown in Table 4.

Example 80

Measurement of anticancer activity

Tumor cells were grown in an RPMI 1640 medium containing of 10% fetal calf serum.

The compound was dissolved in 99.5% ethanol, adjusted before use so that the final concentration of ethanol was 0.1% or less, and added to the medium.

The control was 0.1% ethanol, and L1210 tumor cells were inoculated in the medium in a concentration of $2.5 \times 10^4$ cells/ml and grown for 2 days. The number of surviving cells were measured by trypan blue staining.

The results are shown in Table 4 below.

Example 81

Measurement of bone formation activity

Human osteoblasts (KK-3, 18PDL) were cultured in an α-MEM containing 10% fetal calf serum. After the growth become stationary, the compound was added in a given concentration in the presence of 2 mM α-glycerophosphate and treated for 14 days. The cell phase was washed with physiological saline, and the alkaline phosphatase activity (ALP) was measured through the absorption of $OD_{415}$. Then, calcium (Ca) and phosphorus (P) were extracted with a 2N hydrochloric acid and quantitatively determined. The results are shown in Tables 6 to 9 below.

TABLE 1

| Ex. No. | Starting compound 4-hydroxy-2-cyclopentenone derivative | Aldehyde | 4-hydroxy-2-cyclopentenone derivative | Yield (%) | NMR (δ, CDCl₃) |
|---|---|---|---|---|---|
| 1 | cyclopentenone with Me₃SiO and (CH₂)₄OPh chain | cyclohexyl-CHO | product with cyclohexyl-CH(OH)- substituent | 67 | 0.01(s, 9H), 0.7–1.9(m, 17H), 2.35–2.5(m, 1H), 3.15–3.55(m, 1H), 3.8–3.9(m, 3H), 6.0–6.15(m, 1H), 6.75–6.9(m, 3H), 7.15–7.20(m, 2H), 7.3–7.4(m, 1H) |
| 2 | same cyclopentenone | benzaldehyde | product with Ph-CH(OH)- substituent | 41 | 0.01(s, 9H), 1.2–2.1(m, 6H), 2.3–2.8(m, 1H), 3.0–3.3(m, 1H), 3.8–4.0(m, 2H), 4.9–5.2(m, 1H), 6.0–6.2(m, 1H), 6.7–7.5(m, 11H) |
| 3 | same cyclopentenone | 4-NMe₂-benzaldehyde | product with 4-NMe₂-C₆H₄-CH= substituent | 51 | 0.1(s, 9H), 1.1–2.3(m, 6H), 3.04(s, 3H), 3.05(s, 3H), 3.7–4.0(m, 2H), 6.3–6.4(m, 1H), 6.6–7.0(m, 5H), 7.1–7.4(m, 3H), 7.8–8.2(m, 2H) |
| 4 | same cyclopentenone | pyridine-4-carboxaldehyde | product with pyridyl-CH= substituent | 60 | 0.1(s, 9H), 1.0–2.1(m, 7H), 3.65–3.9(m, 2H), 6.45(d, 1H, J=5.9Hz), 6.77(d, 2H, J=8.2Hz), 6.92(t, 1H J=7.3Hz), 7.1–7.4(m, 2H), 7.28(s, 1H), 7.51(d, 1H, J=6.3 Hz), 7.80(d, 2H, J=6.9 Hz), 8.55(d, 2H, J=6.9Hz) |
| 5 | same cyclopentenone | 4-CO₂Me-benzaldehyde | product with 4-CO₂Me-C₆H₄-CH= substituent | 52 | 0.1(s, 9H), 1.05–2.05(m, 6H), 3.6–3.75(s, 2H), 3.89(s, 3H), 6.44(d, 1H, J=5.9Hz), 6.72(d, 2H, J=7.5Hz), 6.86(t, 1H, J=7.6Hz), 7.15(t, 2H, J=2.0Hz), 7.36(s, 1H), 7.45(d, 1H, J=6.3 Hz), 7.96(s, 4H) |

TABLE 1-continued

| Ex. No. | Starting compound | | 4-hydroxy-2-cyclopentenone derivative | Yield (%) | NMR (δ, CDCl₃) |
|---|---|---|---|---|---|
| | 4-hydroxy-2-cyclopentenone derivative | Aldehyde | | | |
| 6 | (structure) | (structure) | (structure) | 65 | 0.10(s, 9H), 1.05–2.05 (m, 6H), 3.60–3.75(m, 2H), 3.89(s, 3H), 6.44(d, 1H, J=6.9Hz), 6.72(d, 2H, J=7.6Hz), 6.86(t, 1H, J=7.6Hz), 7.15(t, 2H, J=2.0Hz), 7.36(s, 1H), 7.45(d, 1H, J=6.3 Hz), 7.96(s, 4H) |
| 7 | (structure) | (structure) | (structure) | 63 | 0.10(s, 9H), 1.05–2.05 (m, 6H), 3.60–3.75(m, 2H), 3.89(s, 3H), 6.44(d, 1H, J=5.9Hz), 6.72(d, 2H, J=7.6Hz), 6.86(t, 1H, J=7.6Hz), 7.15(t, 2H, J=2.0Hz), 7.36(s, 1H), 7.45(d, 1H, J=6.3 Hz), 7.96(s, 4H) |
| 8 | (structure) | (structure) | (structure) | 48 | 0.09(s, 9H), 0.7–1.0(m, 3H), 1.0–2.4(m, 33H), 6.0–6.5(m, 2H), 7.1–7.4 (m, 1H) |
| 9 | (structure) | (structure) | (structure) | 59 | −0.1(s, 9H), 1.3–2.0(m, 4H), 2.5–2.8(m, 2H), 3.60(s, 3H), 3.82(s, 3H), 6.2–6.4(m, 1H), 6.5–6.9 (m, 3H), 7.0–7.9(m, 5H) |
| 10 | (structure) | (structure) | (structure) | 58 | 0.09(s, 9H), 1.0–2.6(m, 12H), 3.65(s, 3H), 5.07 (s, 2H), 6.3–6.6(m, 1H), 6.9–7.6(m, 9H), 7.85(d, 2H, J=7.0Hz) |

TABLE 1-continued

| Ex. No. | Starting compound | | 4-hydroxy-2-cyclopentenone derivative | Yield (%) | NMR (δ, CDCl₃) |
|---|---|---|---|---|---|
| | 4-hydroxy-2-cyclopentenone derivative | Aldehyde | | | |
| 11 | cyclopentenone with (CH₂)₃-O-THP and Me₃SiO | furfural (OHC-furan) | cyclopentenone with furylmethylene and (CH₂)₃-O-THP, Me₃SiO | 62 | 0.09(s, 9H), 1.2–2.2(m, 12H), 3.2–3.9(m, 4H), 4.5–4.8(m, 1H), 6.2–6.4 (m, 1H), 6.9–7.7(m, 5H) |
| 12 | cyclopentenone with (CH₂)₄-OSiMe₂tBu and Me₃SiO | 4-methoxybenzaldehyde | cyclopentenone with 4-methoxybenzylidene and (CH₂)₄-OSiMe₂tBu, Me₃SiO | 67 | 0.05–0.15(m, 15H), 0.87 (s, 9H), 1.0–2.2(m, 6H), 3.1–3.5(m, 2H), 3.8(s, 3H), 6.2–6.4(m, 2H), 7.0–7.4(m, 4H), 7.85(d, 2H, J=6.7Hz) |
| 13 | cyclopentenone with n-butyl and Me₃SiO | 3,5-difluorobenzaldehyde | cyclopentenone with 3,5-difluorobenzylidene and n-butyl, Me₃SiO | 63 | 0.05(s, 9H), 0.7–1.0(m, 3H), 1.0–2.1(m, 6H), 6.2–6.4(m, 1H), 6.6–6.8 (m, 1H), 7.0–7.6(m, 4H) |
| 14 | cyclopentenone with Me and Me₃SiO | 3,5-dichlorobenzaldehyde | cyclopentenone with 3,5-dichlorobenzylidene and Me, Me₃SiO | 59 | 0.04(s, 9H), 1.52(s, 3H), 6.2–6.5(m, 1H), 6.7–7.5 (m, 5H), 7.95(d, 2H, J= 2.4Hz) |

TABLE 1-continued

| Ex. No. | Starting compound | | 4-hydroxy-2-cyclopentenone derivative | Yield (%) | NMR (δ, CDCl$_3$) |
|---|---|---|---|---|---|
| | 4-hydroxy-2-cyclopentenone derivative | Aldehyde | | | |
| 15 | (cyclopentenone with Me$_3$SiO and t-butylacetylene substituent) | 1-naphthaldehyde | (naphthylmethylene cyclopentenone with Me$_3$SiO and t-butylacetylene) | 39 | 0.10(s, 9H), 1.08(s, 9H), 6.2–6.4(m, 1H), 7.0–8.0 (m, 9H) |
| 16 | (cyclopentenone with Me$_3$SiO and cyclohexyl) | benzaldehyde | (benzylidene cyclopentenone with Me$_3$SiO and cyclohexyl) | 31 | 0.08(s, 9H), 1.0–2.1(m, 11H), 6.2–6.4(m, 1H), 6.6–7.5(m, 5H), 7.8–8.1 (m, 2H) |
| 17 | (cyclopentenone with Me$_3$SiO and (CH$_2$)$_3$OPh) | methyl 4-formylbenzoate | (arylmethylene cyclopentenone with Me$_3$SiO and (CH$_2$)$_3$OPh, CO$_2$Me aryl) | 69 | 1.0–2.1(m, 6H), 3.03(s, 3H), 3.6–3.8(m, 3H), 3.85(s, 3H), 6.3–6.5(m, 1H), 6.6–7.5(m, 7H), 7.7–8.2(m, 4H) |
| 18 | (cyclopentenone with THP-O and (CH$_2$)$_4$OPh) | methyl 4-formylbenzoate | (arylmethylene cyclopentenone with THP-O and (CH$_2$)$_4$OPh, CO$_2$Me aryl) | 63 | 1.0–2.2(m, 12H), 3.2–3.6 (m, 2H), 3.7–3.9(m, 2H), 3.88(s, 3H), 4.5–4.8(m, 1H), 6.3–6.5(m, 1H), 6.7–7.5(m, 7H), 7.7–8.2 (m, 4H) |

TABLE 1-continued

| Ex. No. | Starting compound | | 4-hydroxy-2-cyclopentenone derivative | Yield (%) | NMR (δ, CDCl₃) |
|---|---|---|---|---|---|
| | 4-hydroxy-2-cyclopentenone derivative | Aldehyde | | | |
| 19 | (structure: cyclopentenone with OPh chain, OSiMe₃, Me) | 4-OHC-C₆H₄-CO₂Me | (product structure) | 42 | 0.01(s, 9H), 0.8–1.1(m, 2H), 1.25–1.65(m, 4H), 1.84(d, 2H, J=1.3Hz), 3.65(t, 2H, J=6.0Hz), 3.69(s, 3H), 5.80(d, 1H, J=1.3Hz), 6.6–6.9(m, 3H), 7.0–7.3(m, 3H), 7.79(d, 4H, J=8.3Hz) |
| 20 | (structure with PhO(CH₂)₄, OSiMe₃) | 4-OHC-C₆H₄-CO₂Me | (product structure) | 52 | 0.08(s, 9H), 1.0–2.3(m, 12H), 3.5–3.9(m, 4H), 3.94(s, 3H), 6.03(d, 1H, J=1.5Hz), 6.6–7.4(m, 11H), 7.8–8.0(m, 4H) |
| 21 | (structure with MeO₂C(CH₂)₄, OSiMe₃) | 4-OHC-C₆H₄-CO₂Me | (product structure) | 48 | 0.05(s, 9H), 1.0–2.3(m, 18H), 3.66(s, 3H), 3.7–3.9(m, 2H), 3.90(s, 3H), 5.8–6.1(m, 1H), 6.6–7.5(m, 6H), 7.8–8.1(m, 4H) |
| 22 | (structure with cyclohexyl, OSiMe₃, OPh chain) | 4-OHC-C₆H₄-NO₂ | (product structure) | 72 | 0.09(s, 9H), 1.1–2.4(m, 17H), 3.7–3.9(m, 2H), 5.9–6.2(m, 1H), 6.6–7.5(m, 6H), 7.9–8.4(m, 4H) |
| 23 | (structure with isopropyl, OSiMe₃, isohexyl chain) | 3-OHC-C₆H₄-CF₃ | (product structure) | 63 | 0.08(s, 9H), 0.7–2.4(m, 28H), 5.8–6.1(m, 1H), 6.6–6.9(m, 1H), 7.4–8.2(m, 4H) |

TABLE 1-continued

| Ex. No. | Starting compound | | | Yield (%) | NMR (δ, CDCl₃) |
|---|---|---|---|---|---|
| | 4-hydroxy-2-cyclopentenone derivative | Aldehyde | 4-hydroxy-2-cyclopentenone derivative | | |
| 24 | [structure] | [structure with NBu₂] | [structure] | 47 | 0–0.15(m, 15H), 0.89(s, 9H), 0.7–2.4(m, 42H), 3.2–3.4(m, 4H), 4.5–4.8(m, 1H), 5.4–5.8(m, 2H), 5.8–6.0(m, 1H), 6.6–6.9(m, 3H), 7.8–8.0(m, 2H) |
| 25 | [structure] | [structure with CO₂Me] | [structure] | 50 | 0.06(s, 9H), 1.1–2.2(m, 6H), 3.7–3.85(m, 2H), 3.94(s, 3H), 6.77(d, 2H, J=7.9Hz), 6.91(t, 1H, J=7.8Hz), 7.22(d, 2H, J=7.3Hz), 7.38(s, 1H), 7.52(s, 1H), 8.04(s, 4H) |
| 26 | [structure] | [structure with NMe₂] | [structure] | 75 | 0.10(s, 9H), 1.1–2.3(m, 6H), 3.05(s, 6H), 3.7–3.9(m, 2H), 6.69(d, 2H, J=8.9Hz), 6.79(d, 2H, J=7.9Hz), 6.8–7.0(m, 1H), 7.1–7.3(m, 2H), 7.29(s, 2H), 7.49(s, 1H), 7.91(d, 2H, J=9.2Hz) |
| 27 | [structure] | [structure with CO₂Me] | [structure] | 43 | −0.01(s, 9H), 1.1–2.1(m, 6H), 3.7–3.9(m, 2H), 3.93(s, 3H), 6.30(s, 1H), 6.6–7.0(m, 4H), 7.15–7.4(m, 2H), 7.9–8.2(m, 4H) |
| 28 | [structure] | [pyridine-CHO] | [structure] | 52 | 0.03(s, 9H), 0.7–2.3(m, 18H), 5.0–5.2(m, 1H), 7.36(s, 1H), 7.56(s, 1H), 7.80(d, 2H, J=6.9Hz), 8.57(d, 2H, J=6.8Hz) |

TABLE 1-continued
| Ex. No. | Starting compound 4-hydroxy-2-cyclopentenone derivative | Aldehyde | 4-hydroxy-2-cyclopentenone derivative | Yield (%) | NMR (δ, CDCl₃) |
|---|---|---|---|---|---|
| 29 | 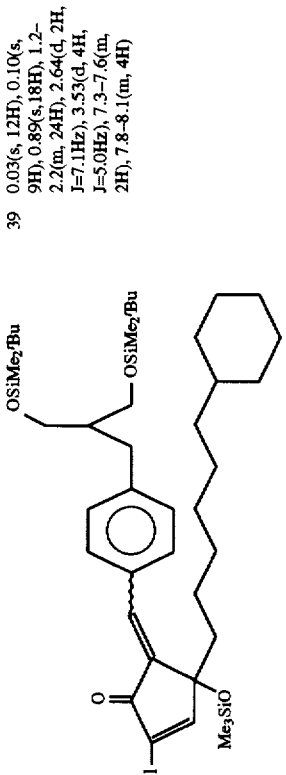 | | | 39 | 0.03(s, 12H), 0.10(s, 9H), 0.89(s,18H), 1.2-2.2(m, 24H), 2.64(d, 2H, J=7.1Hz), 3.53(d, 4H, J=5.0Hz), 7.3-7.6(m, 2H), 7.8-8.1(m, 4H) |
| 30 |  | | | 43 | 0.04(s, 3H), 1.0-2.0(m, 6H), 1.97(s, 3H), 3.7-3.9 (m, 2H), 3.98(s, 3H), 6.7-7.6(m, 6H), 8.01(s, 4H) |
| 31 |  | | | 67 | 0-0.2(m, 6H), 0.89(s, 9H), 3.87(s, 3H), 4.1-4.5 (m, 1H), 6.2-6.4(m, 1H), 6.7-7.0(m, 1H), 7.2-7.5(m, 1H), 7.7-8.1(m, 4H) |
| 32 |  | | | 49 | 0-0.2(m, 6H), 0.90(s, 9H), 2.53(s, 3H), 4.2-4.5 (m, 1H), 7.2-7.9(m, 6H) |
| 33 | 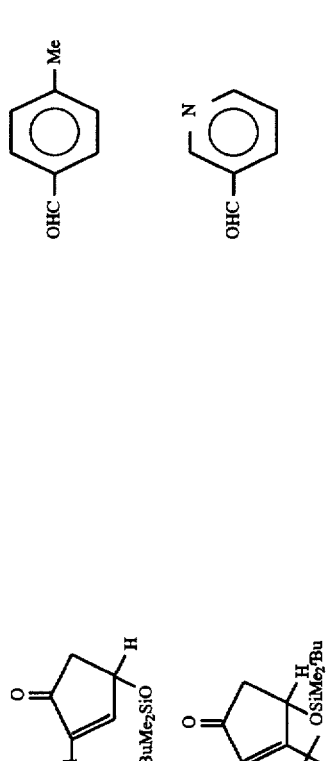 | | | 42 | 0-0.2(m, 6H), 0.89(s, 9H), 1.38(s, 9H), 4.6-5.1 (m, 1H), 5.8-6.1(m, 1H), 6.7-7.0(m, 1H), 7.2-7.4 (m, 2H), 8.4-8.8(m, 1H), 9.03(s, 1H) |

TABLE 2

| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 34 | (structure: cyclopentenone with OH, cyclohexyl, Me₃SiO, (CH₂)₄OPh) | (structure: cyclopentenone with OSO₂Me, cyclohexyl, Me₃SiO, (CH₂)₄OPh) | 30 | 0.01 and 0.05(s, 9H), 1.0–1.8(m, 17H), 2.5–2.9(m, 1H), 3.43(s, 3H), 3.7–3.9(m, 2H), 4.6–4.8(m, 1H), 6.0–6.1(m, 1H), 6.6–6.9(m, 3H), 7.0–7.4(m, 3H) |
| 35 | (structure: cyclopentenone with OSO₂Me, cyclohexyl, Me₃SiO, (CH₂)₄OPh) | (structure: cyclopentenone with exocyclic =CH-cyclohexyl, Me₃SiO, (CH₂)₄OPh) | 28 | 0.01(s, 9H), 1.0–2.05(m, 16H), 3.5–3.6(m, 1H), 3.90(t, 2H, J=6.3Hz), 5.78(d, 1H, J=9.9Hz), 6.24(d, 1H, J=6.3Hz), 6.8–6.95(m, 3H), 7.2–7.3(m, 3H) |
|  |  | (structure: cyclopentenone with exocyclic =CH-cyclohexyl (other isomer), Me₃SiO, (CH₂)₄OPh) | 52 | 0.04(s, 9H), 1.1–2.05(m, 16H), 2.75–2.9(m, 1H), 3.41(t, 2H, J=6.3Hz), 6.34(d, 1H, J=6.3Hz), 6.36(d, 1H, J=11.2Hz), 6.8–6.95(m, 3H), 7.2–7.4(m, 3H) |

TABLE 3

| Ex. No. | Starting compound (4-hydroxy-2-cyclopentenone) | 4-hydroxy-2-cyclopentenone derivative | Yield (%) | NMR (δ, CDCl₃) |
|---|---|---|---|---|
| 36 | *structure* | *structure* | 82 | 0.08(s, 9H), 1.0–1.2(m, 6H), 3.7–3.9(m, 2H), 6.1–6.3(m, 1H), 6.6–7.5(m, 10H), 7.8–8.1(m, 2H) |
| 37 | *structure* | *structure* | 76 | 1.0–2.0(m, 17H), 3.5–3.6(m, 1H), 3.90(t, 2H, J=6.3Hz), 5.98(d, 1H, J=9.9Hz), 6.25(d, 1H, J=6.3Hz), 6.8–7.0(m, 3H), 7.2–7.3(m, 3H) |
| 38 | *structure* | *structure* | 82 | 1.1–2.3(m, 6H), 3.04(s, 3H), 3.05(s, 3H), 3.7–4.0(m, 2H), 6.3–6.4(m, 1H), 6.6–7.0(m, 5H), 7.1–7.4(m, 3H), 7.0–8.2(m, 2H) |
| 39 | *structure* | *structure* | 80 | 1.0–2.1(m, 7H), 3.6–3.9(m, 2H), 6.45(d, 1H, J=6.9Hz), 6.77(d, 2H, J=8.2Hz), 6.92(t, 1H, J=7.3Hz), 7.1–7.4(m, 3H), 7.51(d, 1H, J=6.3Hz), 7.80(d, 2H, J=6.9Hz), 8.55(d, 2H, J=6.9Hz) |
| 40 | *structure* | *structure* | 60 | 1.1–2.1(m, 6H), 2.3(brs), 3.6–3.85(m, 2H), 3.93(s, 3H), 6.47(d, 1H, J=6.0Hz), 6.75(d, 2H, J=7.6Hz), 6.90(t, 1H, J=7.5Hz), 7.22(d, 2H, J=1.7Hz), 7.46(s, 1H), 7.48(s, 1H), 8.02(s, 4H) |
| 41 | *structure* | *structure* | 90 | 1.05–2.15(m, 6H), 2.28(brs, 1H), 3.6–3.85(m, 2H), 3.94(s, 3H), 6.47(d, 1H, J=6.0Hz), 6.76(d, 2H, J=8.0Hz), 6.91(t, 1H, J=7.4Hz), 7.23(d, 2H, J=1.3Hz), 7.45–7.5(m, 2H), 8.03(s, 4H) |

TABLE 3-continued

| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 42 | (structure with CO₂Me-phenyl-OPh chain, Me₃SiO) | (structure with CO₂Me-phenyl-OPh chain, HO) | 87 | 1.05–2.15(m, 6H), 2.22(brs, 1H), 3.6–3.85(m, 2H), 3.94(s, 3H), 6.48(d, 1H, J=5.9Hz), 6.75(d, 2H, J=8.1Hz), 6.91(t, 1H, J=7.4Hz), 7.23(d, 2H, J=1.3Hz), 7.45–7.5(m, 2H), 7.03(s, 4H) |
| 43 | (structure with phenyl-OPh chain, Me₃SiO) | (structure with phenyl-OPh chain, HO) | 78 | 1.0–2.1(m, 6H), 2.7–3.0(m, 1H), 3.7–3.9(m, 2H), 6.1–6.3(m, 1H), 6.6–7.5(m, 10H), 7.8–8.1(m, 2H) |
| 44 | (structure with (CH₂)₃ and alkyl chain, Me₃SiO) | (structure with (CH₂)₃ and alkyl chain, HO) | 79 | 0.7–1.0(m, 3H), 1.0–2.7(m, 34H), 6.0–6.3(m, 1H), 6.4–6.7(m, 1H), 7.2–7.4(m, 1H) |
| 45 | (structure with thiophene-dimethoxyphenyl, Me₃SiO) | (structure with thiophene-dimethoxyphenyl, HO) | 83 | 1.2–2.2(m, 4H), 2.5–3.0(m, 3H), 3.60(s, 3H), 3.79(s, 3H), 6.0–6.2(m, 1H), 6.4–6.9(m, 3H), 7.0–7.9(m, 5H) |
| 46 | (structure with OCH₂Ph-phenyl-CO₂Me chain, Me₃SiO) | (structure with OCH₂Ph-phenyl-CO₂Me chain, HO) | 73 | 1.0–2.6(m, 13H), 3.67(s, 3H), 5.10(s, 2H), 6.3–6.6(m, 1H), 6.9–7.6(m, 9H), 7.95(d, 2H, J=7.5Hz) |

TABLE 3-continued

| Ex. No. | Starting compound (4-hydroxy-2-cyclopentenone derivative) | 4-hydroxy-2-cyclopentenone derivative | Yield (%) | NMR (δ, CDCl$_3$) |
|---|---|---|---|---|
| 47 | (Me$_3$SiO, THP-ether furan structure) | (HO, THP-ether furan structure) | 59 | 1.2–2.3(m, 12H), 2.6(brs, 1H), 3.2–3.9(m, 4H), 4.5–4.8(m, 1H), 6.2–6.4(m, 1H), 6.9–7.7(m, 5H) |
| 48 | (Me$_3$SiO, 4-OMe-phenyl, OSiMe$_2$$^t$Bu) | (HO, 4-OMe-phenyl, OH) | 83 | 1.0–2.6(m, 8H), 3.1–3.5(m, 2H), 3.8(s, 3H), 6.2–6.4(m, 2H), 7.0–7.4(m, 4H), 7.95(d, 2H, J=7.3Hz) |
| 49 | (Me$_3$SiO, 3,5-difluorophenyl) | (HO, 3,5-difluorophenyl) | 62 | 0.7–1.0(m, 3H), 1.0–2.1(m, 6H), 2.6(brs, 1H), 6.2–6.4(m, 1H), 6.6–6.8(m, 1H), 7.0–7.6(m, 4H) |
| 50 | (Me$_3$SiO, Me, 3,5-dichlorophenyl) | (HO, Me, 3,5-dichlorophenyl) | 73 | 1.50(s, 3H), 2.6(brs, 1H), 6.2–6.5(m, 1H), 6.7–7.5(m, 5H), 7.94(d, 2H, J=1.8Hz) |

TABLE 3-continued

| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 51 | [structure: naphthalenylmethylene cyclopentenone with Me₃SiO and tBu-alkynyl] | [structure: naphthalenylmethylene cyclopentenone with HO and tBu-alkynyl] | 41 | 1.12(s, 9H), 2.5(brs, 1H), 6.0–6.2 (m, 1H), 7.0–8.1(m, 9H) |
| 52 | [structure: benzylidene cyclopentenone with Me₃SiO and cyclohexyl] | [structure: benzylidene cyclopentenone with HO and cyclohexyl] | 51 | 1.0–2.5(m, 12H), 6.2–6.4(m, 1H), 6.6–7.5(m, 5H), 7.9–8.2(m, 2H) |
| 53 | [structure with CO₂Me, OPh, OSiMe₃] | [structure with CO₂Me, OPh, OH] | 85 | 0.85–2.2(m, 9H), 2.08(d, 3H, J=1.3 Hz), 3.5–3.7(m, 2H), 4.04(s, 3H), 6.18(d, 1H, J=1.3Hz), 6.6–6.7(m, 2H), 6.7–6.9(m, 1H), 7.1–7.2(m, 2H), 7.35(s, 1H), 7.9–8.0(m, 4H) |
| 54 | [structure with CO₂Me, OPh, PhO(CH₂)₄, OSiMe₃] | [structure with CO₂Me, OPh, PhO(CH₂)₄, OH] | 49 | 1.0–2.3(m, 12H), 2.6–2.8(m, 1H), 3.5–3.9(m, 4H), 3.90(s, 3H), 6.28 (d, 1H, J=1.7Hz), 6.6–7.5(m, 11H), 7.8–8.1(m, 4H) |
| 55 | [structure with CO₂Me, OPh, MeO₂C(CH₂)₅, OSiMe₃] | [structure with CO₂Me, OPh, MeO₂C(CH₂)₅, OH] | 72 | 1.1–2.3(m, 18H), 2.5–2.7(m, 1H), 3.65(s, 3H), 3.7–3.9(m, 2H), 3.92 (s, 3H), 6.1–6.3(m, 1H), 6.6–7.6 (m, 6H), 7.8–8.1(m, 4H) |

TABLE 3-continued
| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 56 | 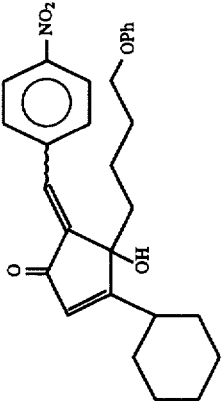 | 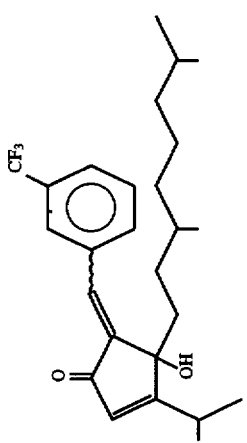 | 58 | 1.1–2.4(m, 17H), 2.5–2.7(m, 1H), 3.7–3.9(m, 2H), 6.2–6.4(m, 1H), 6.6–7.5(m, 6H), 8.0–8.4(m, 4H) |
| 57 | | | 39 | 0.7–2.7(m, 29H), 6.2–6.4(m, 1H), 6.6–6.9(m, 1H), 7.4–8.2(m, 4H) |
| 58 | | | 44 | 0.7–2.7(m, 44H), 3.2–3.4(m, 4H), 4.5–4.8(m, 1H), 5.4–5.9(m, 2H), 6.3–6.5(m, 1H), 6.6–7.0(m, 3H), 7.8–8.0(m, 2H) |
| 59 | 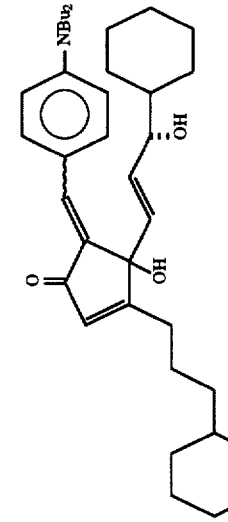 | 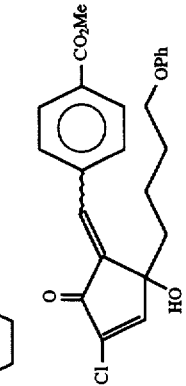 | 93 | 1.1–1.7(m, 4H), 1.95–2.15(m, 2H), 2.6–2.7(m, 1H), 3.7–3.9(m, 2H), 3.94(s, 3H), 6.75(d, 2H, J=7.6Hz), 6.91(t, 1H, J=7.8Hz), 7.22(d, 2H, J=7.6Hz), 7.39(s, 1H), 7.54(s, 1H), 8.02(s, 4H) |

TABLE 3-continued

| Ex. No. | Starting compound (4-hydroxy-2-cyclopentenone derivative) | 4-hydroxy-2-cyclopentenone derivative | Yield (%) | NMR (δ, CDCl$_3$) |
|---|---|---|---|---|
| 60 | (structure with Cl, Me$_3$SiO, NMe$_2$, OPh) | (structure with Cl, HO, NMe$_2$, OPh) | 85 | 1.1–2.3(m, 6H), 3.05(s, 6H), 3.7–3.9(m, 2H), 6.69(d, 2H, J=8.9Hz), 6.79(d, 2H, J=7.9Hz), 6.8–7.0(m, 1H), 7.1–7.3(m, 2H), 7.29(s, 1H), 7.49(s, 1H), 7.91(d, 2H, J=9.2Hz) |
| 61 | (structure with F, Me$_3$SiO, CO$_2$Me, OPh) | (structure with F, HO, CO$_2$Me, OPh) | 61 | 1.1–2.1(m, 6H), 2.6–2.8(m, 1H), 3.7–3.9(m, 2H), 3.92(s, 2H), 6.25(s, 1H), 6.6–7.0(m, 4H), 7.15–7.4(m, 2H), 7.9–8.2(m, 4H) |
| 62 | (structure with Cl, Me$_3$SiO, pyridine) | (structure with Cl, HO, pyridine) | 71 | 0.7–2.3(m, 18H), 2.6–2.8(m, 1H), 5.0–5.2(m, 1H), 7.35(s, 1H), 7.55(s, 1H), 7.81(d, 2H, J=6.9Hz), 8.57(d, 2H, J=6.9Hz) |
| 63 | (structure with Cl, Me$_3$SiO, OSiMe$_2$$^t$Bu, cyclohexyl) | (structure with Cl, HO, OH, cyclohexyl) | 46 | 1.0–2.2(m, 24H), 2.4–2.7(m, 2H), 3.4–4.0(m, 6H), 7.3–7.6(m, 2H), 7.8–8.1(m, 4H) |
| 64 | (structure with Cl, OSiMe$_3$, CO$_2$Me, OPh) | (structure with Cl, HO, CO$_2$Me, OPh) | 61 | 1.0–2.1(m, 6H), 1.93(s, 3H), 2.6–2.7(m, 1H), 3.7–3.9(m, 2H), 3.97(s, 3H), 6.7–7.6(m, 6H), 8.02(s, 4H) |

TABLE 3-continued

| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 65 | [structure: 4-CO₂Me-benzylidene cyclopentenone with OSiMe₂ⁿBu] | [structure: 4-CO₂Me-benzylidene cyclopentenone with OH] | 52 | 2.7–3.1(m, 1H), 3.91(s, 3H), 4.7–5.1(m, 1H), 6.2–6.4(m, 1H), 6.7–7.0(m, 1H), 7.2–7.6(m, 1H), 7.8–8.2(m, 1H) |
| 66 | [structure: 4-Me-benzylidene chlorocyclopentenone with OSiMe₂ⁿBu] | [structure: 4-Me-benzylidene chlorocyclopentenone with OH] | 63 | 2.43(s, 3H), 2.7–3.0(m, 1H), 4.3–4.6(m, 1H), 7.2–7.9(m, 6H) |
| 67 | [structure: pyridylmethylene cyclopentenone with ⁿBu and OSiMe₂ⁿBu] | [structure: pyridylmethylene cyclopentenone with ⁿBu and OH] | 43 | 1.35(s, 9H), 2.4–2.7(m, 1H), 4.5–5.0(m, 1H), 6.2–6.4(m, 1H), 6.7–7.0(m, 1H), 7.2–7.4(m, 2H), 8.4–8.8(m, 2H), 9.01(s, 1H) |
| 68 | [structure: cyclohexyl OAc with OPh chain, OSiMe₃] | [structure: cyclohexyl OAc with OPh chain, OH] | 78 | 0.7–2.0(m, 17H), 2.05(s, 3H), 3.1–3.4(m, 1H), 3.7–3.9(m, 2H), 4.0–4.2(m, 1H), 6.0–6.2(m, 1H), 6.7–7.0(m, 3H), 7.1–7.4(m, 3H) |
| 69 | [structure: phenyl OAc with OPh chain, OSiMe₃] | [structure: phenyl OAc with OPh chain, OH] | 68 | 1.0–2.1(m, 6H), 2.07(s, 3H), 2.7–3.0(m, 1H), 3.0–3.3(m, 1H), 3.8–4.0(m, 2H), 5.8–6.0(m, 1H), 6.0–6.2(m, 1H), 6.7–7.5(m, 11H) |

TABLE 3-continued
| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 70 | 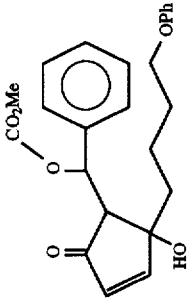 | | 41 | 1.1–1.2(m, 6H), 2.7–3.0(m, 1H), 3.0–3.3(m, 1H), 3.83(s, 3H), 3.7–3.9(m, 2H), 5.6–5.9(m, 1H), 6.0–6.2(m, 1H), 6.7–7.5(m, 11H) |

TABLE 4

| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 71 | | | 49 | 0.08(s, 9H), 0.7–2.0(m, 17H), 2.04 (s, 3H), 3.1–3.5(m, 1H), 3.7–3.9 (m, 2H), 4.0–4.2(m, 1H), 6.0–6.2 (m, 1H), 6.7–6.9(m, 3H), 7.1–7.4 (m, 3H) |
| 72 | | | 43 | 0.03(s, 9H), 1.1–2.1(m, 6H), 2.07 (s, 3H), 3.0–3.3(m, 1H), 3.8–4.0 (m, 2H), 5.8–6.0(m, 1H), 6.0–6.2 (m, 1H), 6.7–7.5(m, 11H) |
| 73 | | | 32 | 1.0–2.1(m, 6H), 2.01(s, 3H), 2.05 (s, 3H), 3.80(s, 3H), 3.95–4.1(m, 2H), 6.2–6.4(m, 2H), 7.0–7.4(m, 4H), 7.8–8.1(m, 2H) |
| 74 | | | 27 | 0.05(s, 9H), 1.1–2.1(m, 6H), 3.0–3.3(m, 1H), 3.82(s, 3H), 3.7–3.9 (m, 2H), 5.6–5.9(m, 1H), 6.0–6.2 (m, 1H), 6.7–7.5(m, 11H) |
| 75 | | | 68 | 1.0–2.6(m, 7H), 3.82(s, 3H), 4.3–4.5(m, 2H), 6.2–6.4(m, 2H), 7.0–7.6(m, 7H), 7.8–8.1(m, 4H) |

TABLE 4-continued

| Ex. No. | Starting compound (4-hydroxy-2-cyclopentenone derivative) | 4-hydroxy-2-cyclopentenone derivative | Yield (%) | NMR (δ, CDCl₃) |
|---|---|---|---|---|
| 76 | [structure with MeO₂C(CH₂)₆, OPh, CO₂Me] | [structure with HO₂C(CH₂)₆, OPh, CO₂Me] | 72 | 1.1–2.3(m, 18H), 2.6–2.9(m, 2H), 3.7–3.9(m, 2H), 3.91(s, 3H), 6.2–6.4(m, 1H), 6.6–7.6(m, 6H), 7.8–8.1(m, 4H) |
| 77 | [structure with OCH₂Ph, CO₂Me] | [structure with OCH₂Ph, CO₂H] | 63 | 1.0–2.8(m, 14H), 5.07(S, 2H), 6.3–6.5(m, 1H), 6.9–7.6(m, 9H), 7.8–8.1(m, 2H) |
| 78 | [structure with OCH₂Ph, CO₂H] | [structure with OCH₂Ph, CO–N thiazolidinethione] | 60 | 1.0–2.3(m, 12H), 2.5–2.7(m, 1H), 3.1–3.4(m, 2H), 4.3–4.6(m, 2H), 5.10(s, 2H), 6.2–6.4(m, 1H), 6.9–7.6(m, 9H), 7.8–8.1(m, 2H) |
| 79 | [structure with OCH₂Ph, CO–N thiazolidinethione] | [structure with OCH₂Ph, CO–O sugar] | 32 | 1.0–2.9(m, 11H), 3.0–5.3(m, 13H), 6.3–6.6(m, 1H), 6.9–7.6(m, 9H), 7.9–8.1(m, 2H) |

TABLE 5
| Tested compound | IC$_{50}$ (μg/ml) |
|---|---|
| 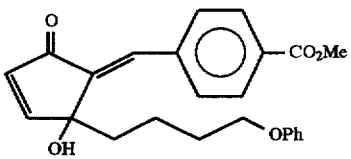 | 0.014 |
| 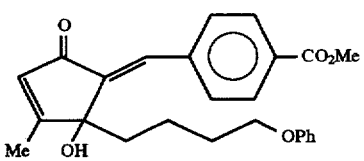 | 10.77 |
| 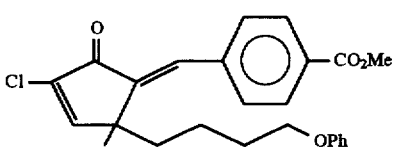 | 0.004 |
TABLE 5-continued
| Tested compound | IC$_{50}$ (μg/ml) |
|---|---|
| 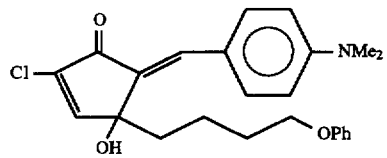 | 0.062 |
| 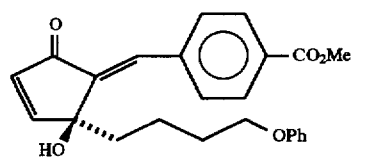 | 0.010 |
| 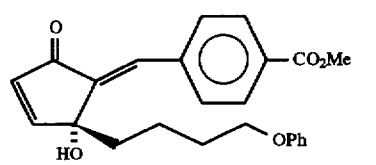 | 0.026 |
TABLE 6
| 4-hydroxy-2-cyclopentenone derivative | | Ca μg/dish | P μg/dish | ALP OD$_{415}$/dish |
|---|---|---|---|---|
| 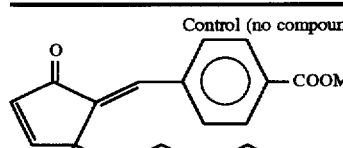 | Control (no compound) | 11.00 ± 1.73 | 20.00 ± 1.73 | 0.550 ± 0.040 |
| | 2.5 × 10$^{-7}$M | 22.67 ± 3.51 | 28.33 ± 2.52 | 0.572 ± 0.028 |
| | 1.0 × 10$^{-6}$M | 47.00 ± 1.00 | 41.33 ± 0.58 | 0.488 ± 0.044 |
| 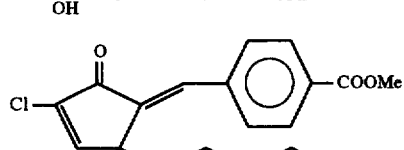 | 2.5 × 10$^{-7}$M | 37.00 ± 1.00 | 36.00 ± 1.00 | 0.484 ± 0.078 |
| | 1.0 × 10$^{-6}$M | 124.50 ± 2.12 | 77.50 ± 0.71 | 0.0 |
TABLE 5-continued
| Tested compound | IC$_{50}$ (μg/ml) |
|---|---|
| 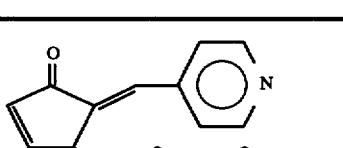 | 0.021 |
| 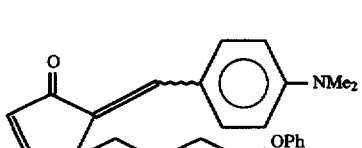 | 0.378 |

TABLE 7

| 4-hydroxy-2-cyclopentenone derivative | | Ca μg/dish | P μg/dish | ALP OD$_{415}$/dish |
|---|---|---|---|---|
| Control (no compound) | | 0.33 ± 0.29 | 0.17 ± 0.29 | 0.826 ± 0.006 |
|  | $10^{-7}$M | 0.0 ± 0 | 0.33 ± 0.29 | 0.796 ± 0.047 |
| | $10^{-6}$M | 23.50 ± 3.77 | 1.72 ± 0.05 | 0.503 ± 0.033 |

TABLE 8

| 4-hydroxy-2-cyclopentenone derivative | | Ca μg/dish | P μg/dish | ALP OD$_{415}$/dish |
|---|---|---|---|---|
| Control (no compound) | | 0.33 ± 0.58 | 7.67 ± 0.58 | 1.684 ± 0.068 |
| | $10^{-5}$M | 1.00 ± 0.0 | 8.33 ± 1.53 | 1.538 ± 0.028 |
| | $10^{-4}$M | 8.133 ± 3.06 | 50.33 ± 1.53 | 0.697 ± 0.10 |

TABLE 9

| 4-hydroxy-2-cyclopentenone derivative | | Ca μg/dish | P μg/dish | ALP OD$_{415}$/dish |
|---|---|---|---|---|
| Control (no compound) | | 2.17 ± 2.56 | 3.83 ± 1.72 | 1.15 ± 0.19 |
| | $1.0 \times 10^{-6}$M | 18.00 ± 8.00 | 13.00 ± 4.69 | 0.74 ± 0.06 |
| | $3.3 \times 10^{-6}$M | 318.50 ± 12.50 | 178.00 ± 11.80 | 1.79 ± 0.05 |
| | $1.0 \times 10^{-6}$M | 312.17 ± 12.30 | 170.33 ± 11.60 | 0.04 ± 0.01 |
| | $3.3 \times 10^{-6}$M | 328.00 ± 15.90 | 184.83 ± 14.20 | 0.03 ± 0.00 |

INDUSTRIAL APPLICABILITY

The optically active 4-hydroxy-2-cyclopentenone derivatives and the mixtures thereof according to the present invention exhibit a strong effect of inhibiting the growth of L1210 leukemia cells at a low concentration and therefore, can be considered for use as an anticancer agent. Further, these compounds enhances the content of calcium and phosphorus in the human osteoblasts. Accordingly, these compounds are useful as a bone formation accelerator and are effective for the treatment or prevention of osteoporosis, osteomalacia, etc. Further, the compounds of the present invention can be expected to have an antiviral activity and an antimicrobial activity, which renders the compound of the present invention very useful as a pharmaceutical.

We claim:

1. An optically active 4-hydroxy-2-cyclopentenone compound having formula (I):

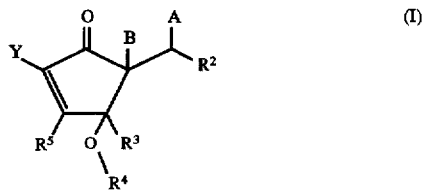

wherein Y is a hydrogen atom or a halogen atom; A and B are such that B is a hydrogen atom and A is selected from the group consisting of a hydroxyl group, a $C_2$–$C_7$ acyloxyl group, a $C_2$–$C_5$ alkoxycarbonyloxyl group and a $C_1$–$C_7$ sulfonyloxy group or A and B together form a single bond; $R^2$ is substituted or unsubstituted and is selected from the group consisting of (i) a $C_4$–$C_{10}$ alicyclic hydrocarbon group, (ii) a $C_6$–$C_{10}$ aromatic hydrocarbon group and (iii) a $C_1$–$C_9$ aromatic heterocyclic group; $R^3$ is substituted or unsubstituted and is selected from the group consisting of (i) a $C_1$–$C_{10}$ aliphatic hydrocarbon group, (ii) a $C_4$–$C_{10}$ alicyclic hydrocarbon group and (iii) a $C_6$–$C_{10}$ aromatic hydrocarbon group; $R_4$ is a hydrogen atom, a $C_1$–$C_4$ alkyl group, a $C_2$–$C_7$ acyl group, a $C_2$–$C_5$ alkoxycarbonyl group, a tri ($C_1$–$C_7$) hydrocarbon silyl group and a group forming an acetal bond together with the oxygen atom to which $R_4$ is bonded; $R^5$ is substituted or unsubstituted and is selected from the group consisting of (i) a $C_1$–$C_{10}$ aliphatic hydrocarbon group, (ii) a $C_4$–$C_{10}$ alicyclic hydrocarbon group and (iii) a hydrogen atom, and mixtures thereof.

2. An optically active 4-hydroxy-2-cyclopentenone compound as claimed in claim 1 having formula (I-1):

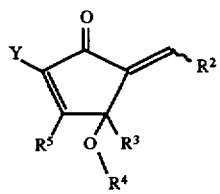

(I-1)

wherein Y, $R^2$, $R^3$, $R^4$, and $R^5$ are the same as defined above and the wavy line ∿ shows that the substituent bonding with the double bond is an E configuration or Z configuration or a mixture of these in any ratio.

3. An optionally active 4-hydroxy-2-cyclopentenone compound as claimed in claim 1,

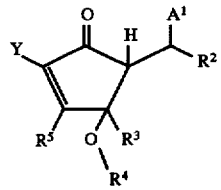

(I-2)

wherein $A^1$ is selected from the group consisting of a hydroxyl group, a $C_2$–$C_7$ acyloxyl group, a $C_2$–$C_5$ alkoxycarbonyl group and a $C_1$–$C_7$ sulfonyloxyl group and Y, $R^2$, $R^3$, $R^4$, and $R^5$ are the same as defined above.

4. An optically active 4-hydroxy-2-cyclopentenone compound as claimed in claim 1, wherein Y is a hydrogen atom or a chlorine atom in the above formula (I).

5. An optically active 4-hydroxy-2-cyclopentenone compound as claimed in claim 1, wherein $R^2$ is a substituted or unsubstituted $C_6$–$C_{10}$ aromatic hydrocarbon group in the above formula (I).

6. An optically active 4-hydroxy-2-cyclopentenone compound as claimed in claim 1, wherein $R^3$ is a substituted or unsubstituted $C_1$–$C_{10}$ aliphatic hydrocarbon group in the above formula (I).

7. An optically active 4-hydroxy-2-cyclopentenone compound as claimed in claim 1, wherein $R^5$ is a hydrogen atom in the above formula (I).

8. An optically active 4-hydroxy-2-cyclopentenone compound as claimed in claim 1, wherein $R^4$ is a hydrogen atom in the above formula (I).

9. An anticancer agent comprising, as an effective active ingredient at least one optically active 4-hydroxy-2-cyclopentenone compound having formula (I) in claim 1 and a pharmaceutically acceptable carrier.

10. A method of accelerating bone formation comprising administering, as an effective active ingredient, at least one optically active 4-hydroxy-2-cyclopentenone compound having formula (I):

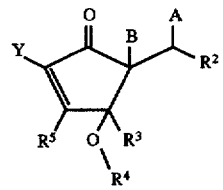

(I)

wherein Y is a hydrogen atom or a halogen atom; A and B are such that B is a hydrogen atom and A is selected from the group consisting of a hydroxyl group, a $C_2$–$C_7$ acyloxyl group, a $C_2$–$C_5$ alkoxycarbonyloxyl group and a $C_1$–$C_7$ sulfonyloxy group or A and B together form a single bond; $R^2$ is substituted or unsubstituted and is selected from the group consisting of (i) a $C_4$–$C_{10}$ alicyclic hydrocarbon group, (ii) a $C_6$–$C_{10}$ aromatic hydrocarbon group and (iii) a $C_1$–$C_9$ aromatic heterocyclic group; $R^3$ is substituted or unsubstituted and is selected from the group consisting of (i) a $C_1$–$C_{10}$ aliphatic hydrocarbon group, (ii) a $C_4$–$C_{10}$ alicyclic hydrocarbon group and (iii) a $C_6$–$C_{10}$ aromatic hydrocarbon group; $R_4$ is a hydrogen atom, a $C_1$–$C_4$ alkyl group, a $C_2$–$C_7$ acyl group, a $C_2$–$C_5$ alkoxycarbonyl group, a tri ($C_1$–$C_7$) hydrocarbon silyl group and a group forming an acetal bond together with the oxygen atom to which $R_1$ is bonded; $R^5$ is substituted or unsubstituted and is selected from the group consisting of (i) a $C_1$–$C_{10}$ aliphatic hydrocarbon group, (ii) a $C_4$–$C_{10}$ alicyclic hydrocarbon group and (iii) a hydrogen atom, and mixtures thereof, and a pharmaceutically acceptable carrier.

\* \* \* \* \*